US012708713B2

(12) United States Patent
Troebner et al.

(10) Patent No.: US 12,708,713 B2
(45) Date of Patent: Aug. 18, 2026

(54) INJECTION DEVICE WITH AN ELECTRONIC DETECTOR

(71) Applicant: Sanofi, Paris (FR)

(72) Inventors: Philipp Troebner, Frankfurt am Main (DE); Stefan Alt, Frankfurt am Main (DE); Thomas Klemm, Frankfurt am Main (DE); Patrick Steiner, Frankfurt am Main (DE); Philipp Mueller, Wil (CH); Martin Rebmann, Wil (CH)

(73) Assignee: SANOFI, Paris (FR)

( * ) Notice: Subject to any disclaimer, the term of this patent is extended or adjusted under 35 U.S.C. 154(b) by 689 days.

(21) Appl. No.: 17/920,113

(22) PCT Filed: Apr. 23, 2021

(86) PCT No.: PCT/EP2021/060630
§ 371 (c)(1),
(2) Date: Oct. 20, 2022

(87) PCT Pub. No.: WO2021/214274
PCT Pub. Date: Oct. 28, 2021

(65) Prior Publication Data

US 2023/0166045 A1 Jun. 1, 2023

(30) Foreign Application Priority Data

Apr. 23, 2020 (EP) .................................... 20315211

(51) Int. Cl.

| | |
|---|---|
| ***A61M 5/315*** | (2006.01) |
| ***A61M 5/20*** | (2006.01) |
| ***A61M 5/24*** | (2006.01) |

(52) U.S. Cl.
CPC .......... *A61M 5/31551* (2013.01); *A61M 5/20* (2013.01); *A61M 5/24* (2013.01);
(Continued)

(58) Field of Classification Search
CPC ...... A61M 5/31551; A61M 5/20; A61M 5/24; A61M 5/31568; A61M 2205/50; A61M 2205/3561; A61M 2205/8206
See application file for complete search history.

(56) References Cited

U.S. PATENT DOCUMENTS

| | | | |
|---|---|---|---|
| 2003/0040716 | A1 | 2/2003 | Heiniger et al. |
| 2012/0204662 | A1 | 8/2012 | Matthias et al. |

(Continued)

FOREIGN PATENT DOCUMENTS

| | | | |
|---|---|---|---|
| CN | 106029131 | A | 10/2016 |
| CN | 106456902 | A | 2/2017 |

(Continued)

OTHER PUBLICATIONS

First Office Action, CN Patent Application No. 202180029556.1, dated Feb. 28, 2025, pp. 1-19 (with pp. 1-9 being a translation).

(Continued)

*Primary Examiner* — Tasnim Mehjabin Ahmed
(74) *Attorney, Agent, or Firm* — Bond, Schoeneck & King, PLLC

(57) ABSTRACT

The present disclosure relates to an injection device for administering of a dose of a medicament. The injection device includes a housing that configured to accommodates a cartridge filled with the medicament, a first component movable relative to the housing along the longitudinal direction between an initial position and a trigger position for dispensing of the dose of the medicament, a second component rotatable relative to the housing for at least one of setting of the dose or dispensing of the dose, a cavity provided in or formed by at least one of the first component and the second component, the cavity been sized to accommodate an electronic detector, and at least a first gasket fastened to one of the housing, the first component and the second component and configured to seal the cavity against
(Continued)

ingress of impurities at least while the first component is in the initial position.

20 Claims, 8 Drawing Sheets

(52) U.S. Cl.
CPC . *A61M 5/31568* (2013.01); *A61M 2205/3561* (2013.01); *A61M 2205/50* (2013.01); *A61M 2205/8206* (2013.01)

(56) References Cited

U.S. PATENT DOCUMENTS

| | | | | |
|---|---|---|---|---|
| 2018/0147362 | A1 | 5/2018 | Arenas Latorre et al. | |
| 2019/0217016 | A1 | 7/2019 | Rehbein | |
| 2020/0114087 | A1* | 4/2020 | Bauer | A61M 5/31551 |
| 2020/0230325 | A1* | 7/2020 | Bengtsson | A61M 5/31568 |

FOREIGN PATENT DOCUMENTS

| | | | |
|---|---|---|---|
| CN | 108025139 | A | 5/2018 |
| CN | 110035781 | A | 7/2019 |
| CN | 110461392 | A | 11/2019 |
| WO | WO 2004/078239 | | 9/2004 |
| WO | WO 2004/078240 | | 9/2004 |
| WO | WO 2004/078241 | | 9/2004 |
| WO | WO 2014/033195 | | 3/2014 |
| WO | 2015187913 | A1 | 12/2015 |
| WO | 2018060023 | A1 | 4/2018 |
| WO | 2018134385 | A1 | 7/2018 |
| WO | WO 2019/101962 | | 5/2019 |
| WO | 2019149868 | A1 | 8/2019 |
| WO | WO 2019/164955 | | 8/2019 |

OTHER PUBLICATIONS

International Preliminary Report on Patentability in International Appln. No. PCT/EP2021/060630, mailed on Nov. 3, 2022, 11 pages.
International Search Report and Written Opinion in International Appln. No. PCT/EP2021/060630, mailed on Jun. 4, 2021, 14 pages.

* cited by examiner 212
420
400
200
112
100
90
300
110
32
10
210
150

212
420
400
200
112
100
90
302
300
11
110
32
10
210
12
150

212
400
200
112
100
90
300
304
110
32
10
210
150

212
400
200
112
100
90
304
300
11
110
32
10
210
12
150

INJECTION DEVICE WITH AN ELECTRONIC DETECTOR

CROSS REFERENCE TO RELATED APPLICATIONS

The present application is the national stage entry of International Patent Application No. PCT/EP2021/060630, filed on Apr. 23, 2021, and claims priority to Application No. EP 20315211.1, filed on Apr. 23, 2020, the disclosures of which are incorporated herein by reference.

TECHNICAL FIELD

The present disclosure relates to the field of drug delivery devices for administering of a dose of a medicament. The disclosure particularly relates to a drug delivery device provided with and/or configured for cooperation with an electronic detector for acquisition of injection related information during use of the injection device.

BACKGROUND

Drug delivery devices for setting and dispensing a single or multiple doses of a medicament are as such well-known in the art. Generally, such devices may have substantially a similar purpose as that of an ordinary syringe.

Drug delivery devices, such as injection or inhaling devices, e.g. pen-type injectors, have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Such injection devices should provide setting and subsequent dispensing of a dose of a medicament of variable size. Moreover, a dose setting as well as a dose dispensing procedure must be easy to operate and has to be unambiguous.

The medicament to be dispensed or expelled by the drug delivery device may be provided and contained in a multi-dose cartridge. Such cartridges typically comprise a vitreous barrel sealed in distal direction by means of a pierceable seal and being further sealed in proximal direction by the bung. With reusable drug delivery devices an empty cartridge is replaceable by a new one. In contrast to that, drug delivery devices of disposable type are readily equipped with such a cartridge. They are to be entirely discarded when the medicament in the cartridge has been dispensed or used-up.

With some drug delivery devices, such as pen-type injection devices a user has to set a dose of equal or variable size by rotating a dose dial in a clockwise or dose-incrementing direction relative to a body or housing of the injection device. For injecting and expelling of a dose of a liquid medicament the user has to depress a trigger or dose button in a distal direction and hence towards the body or housing of the injection device. Typically, the user uses his thumb for exerting a distally directed pressure onto the dose button, which is located at a proximal end of the dose dial and the dose dial sleeve, while holding the housing of the injection device with the remaining fingers of the same hand.

For mechanically implemented injection devices it is desirable to enable a precise, reliable and quasi-automated supervision and/or collection of injection-related data during use of the injection device. Mechanically operated injection devices may be equipped with an electronically implemented add-on device or data logging device configured to monitor user-induced operation of the injection device.

Some data logging devices may be configured for attachment to an injection device. Some data logging device may be embedded or arranged in the injection device. Other drug delivery devices may be implemented electronically, hence they comprise an integrated electronic unit configured for and operable to monitor operation of the drug delivery device over time. Here, the data logging device is provided by the integrated electronic unit.

Administration details and patient specific data can be logged and stored in such data logging devices during repeated use of the respective drug delivery device. It is generally desirable to obtain access to the respective data as stored in the data logging device, e.g. for patient supervision and/or for optimizing a long-term therapy. The data logging device may be configured to establish a communication link with an external electronic device. The communication link may be of wireless or wired type.

With any type of data logging device suitable for use with a drug delivery device, such as a pen-type injector a relative movement of at least two components of the injection device must be quantitatively detected or measured.

With some injection devices at least two selected components of the injection device are subject to a longitudinal and/or rotational movement relative to each other. Such a relative movement may occur during setting of a dose of a medicament or during dispensing of the respective dose. With some devices a user is given the possibility to set or to select a dose of variable size, e.g. by rotating a dose dial, e.g. provided at or near a proximal longitudinal end of the injection device. Setting of a dose, e.g. dialing of the dose dial, may lead to a rotation of a number sleeve located inside the housing of the injection device. The number sleeve, typically provided with a sequence of dose indicating numbers may be subject to a rotational and/or to a helical motion relative to a housing of the injection device.

The housing of the injection device may comprise a dosage window, in which a portion of the number sleeve reveals. With some examples of injection devices, the number sleeve is part of a dial extension. With this type of injection devices, the dial extension and the number sleeve are subject to a longitudinal displacement relative to the housing or body of the injection device during both, setting of a dose and dispensing of the dose. For setting of a dose, dialing of the dose dial leads to a combined rotational and longitudinal motion of the number sleeve and of the dial extension relative to the housing of the injection device. Typically, the dial extension starts to move in longitudinal proximal direction relative to the body or housing of the injection device.

For dispensing of a dose, numerous injection devices provide a dose button or a trigger button at the proximal end of the housing of the injection device or at a proximal end of the dial extension. By depressing the trigger or trigger button in distal direction, a clutch of a drive mechanisms of such injection devices is engaged and/or disengaged with or from further components of the drug delivery device, thereby switching the injection device into a dispensing mode or dispensing configuration. A force exerted by the user onto the trigger in distal direction may cause a return of the dial extension back into the initial position. Such a return motion may be accompanied by a respective rotation of the number sleeve.

For measuring or determining of a size of a dose quantitatively the amount of relative movement between at least a first and a second component of the injection device has to be measured or determined during setting of a dose and/or during dispensing of the dose.

For measuring of a size of a dose actually set or dispensed by an injection device, e.g. by a pen-type injector there may be provided an electronic detector or an electronic detection unit typically equipped with a sensor attached to e.g. a first component and equipped with a scale or code attached to the second component. During dose setting or during dose dispensing the first component may be subject to a longitudinal and/or rotational movement relative to the second component. Hence, the electronic sensor of the electronic detector and the associated code will be subject to a measurable movement relative to each other.

Such electronic detectors can be implemented in many different ways. A sensor of the electronic detector may comprise one of a switch, a magnetic sensor, an optical sensor a capacitive sensor, an acoustic sensor, such as a microphone, an inductive sensor and many other types of sensors. Some of the generally available sensor techniques may operate contact less. Generally, the electronic components of such electronic detectors should be protected against environmental influences or hazards. This may particularly apply to e.g. optically implemented sensors, which require a rather clean environment between the electronic sensor and a corresponding optical code.

Wrapping of the electronic sensor inside a cover, envelope or wrap may be detrimental to the sensitivity and precision of the measurement provided by the electronic detector. Since the mutually corresponding components of the electronic detector, hence the electronic sensor and the corresponding code have to be provided on separate and mutually displaceable components of e.g. a drive mechanism of the injection device that are subject to a relative movement during dose setting or dose dispensing the possibilities to wrap the entire electronic detector in a cover or wrap are somewhat limited.

Especially with optically implemented electronic sensors the wrapping of an optical detector or sensor may come along with internal reflections or absorption at the wrap or cover, which absorption or reflection may have a further impact on the operation and signal generation of the respective optical sensor.

SUMMARY

This disclosure relates to an improved injection device suitable for an electronic detector or equipped with an electronic detector, wherein on the one hand the electronic detector is effectively protected against environmental influences or hazards and wherein on the other hand the protection of the electronic sensor has no or only little influence on the operability, precision or long-term stability of the electronic sensor.

The injection device can provide an optimal balance between a precise and reliable operation of the electronic sensor and an effective protection of the electronic sensor, in particular against humidity, dust or other impurities.

In one aspect, an injection device for administering or dispensing of a dose of a medicament comprises a housing extending along a longitudinal direction. The housing is configured to accommodate a cartridge filled with the medicament. The injection device further comprises a drive mechanism configured to operably engage with the cartridge, typically with a bung of the cartridge, for dispensing of the dose of the medicament.

The injection device further comprises a first component movable relative to the housing along the longitudinal direction between an initial position and a trigger position for dispensing of the dose of the medicament. The injection device further comprises a second component. The second component is rotatable relative to the housing for at least one of setting of the dose and dispensing of the dose. Furthermore, the injection device comprises a cavity. The cavity is provided in at least one of the first component and the second component or the cavity is formed by at least one of the first component and the second component. The cavity is sized to accommodate an electronic detector. The cavity may be also closed or covered by at least one of the first component and the second component.

One of the first component and the second component is configured for attachment of the electronic detector. The electronic detector is configured to recognize or to detect a code provided on the other one of the first component and the second component. There is provided at least a first gasket fastened to one of the housing, the first component and the second component. The gasket is configured to seal the cavity against ingress of impurities at least while the first component is in the initial position.

The gasket provides a sealing of the cavity against the environment and effectively prevents ingress of any impurities, such as humidity or dust into the cavity, in which the electronic detector and the code are provided. In this way and as long as the first component is and remains in the initial position, the cavity is effectively sealed and any impurities in the surrounding of the injection device are effectively hindered to enter the cavity. In this way, the electronic detector, in particular the electronic sensor of the detector as well as the code can be effectively protected against impurities, such as dust or humidity.

It may be only upon moving of the first component from the initial position towards and into the trigger position, that the seal provided by the at least first gasket is temporally abrogated. Here it should be taken into account, that most of the time the injection device is not in use. It may be stored e.g. in a refrigerated area and a user of the injection device may use the respective device for injection of only once, twice or three times daily for a comparatively limited amount of time. Moreover, during an injection procedure, the injection device is typically used in a comparatively clean if not sterile environment. Hence, the total time the injection device is typically in use, e.g. for setting and dispensing of a dose compared to the overall lifetime of such an injection device is comparatively short.

It is hence tolerable to abrogate the seal of the cavity during dose setting and/or during dose dispensing. In the initial position of the first component the cavity is effectively sealed against the environment by the at least first gasket. During setting of a dose and/or during dispensing of a dose, the seal as provided by the first gasket between at least two of the housing, the first component and the second component is temporally abrogated, thus supporting and allowing a movement of at least one of the first component and the second component relative to the other one of the first component and the second component and/or relative to the housing.

With some examples, the injection device comprises the electronic detector arranged inside the cavity. The economic detector is arranged or fixed to one of the first component and the second component. The code cooperating with the electronic detector is arranged or fixed to the other one of the first component and the second component.

With typical examples, the first component can be implemented as a trigger of the injection device. The first component may be located at a proximal longitudinal end of the injection device. The second component can be implemented as a dose dial either rotationally supported at a proximal end of the housing of the injection device or implemented as a component of a dial extension of the injection device. When the injection device is equipped with a dial extension configured to move proximally relative to the housing during a dose incrementing dose setting operation and being configured for distally directed displacement relative to the housing during and for dose dispensing, both, the first component and the second component may be arranged on the dial extension and/or may be supported by the dial extension.

With other examples, the first component may be fixed to the housing with regard to the longitudinal direction. It may be only rotationally movable relative to the housing. Here, the first component may be displaceable relative to the housing as well as relative to the second component between the initial position and the trigger position. Typically, the trigger position is located distally from the initial position. The first component may be realized by a spring element configured to bias the first component in the initial position, which may be a proximal end position of the first component.

With some examples, e.g. when the injection device is equipped with a dial extension the at least first gasket may be provided between the housing and the second component. In an initial configuration the gasket may be squeezed in longitudinal direction between the second component and the housing. As the second component is subject to a dose incrementing movement and is hence subject to a proximally directed displacement relative to the housing, the sealing provided by the gasket may be temporally abrogated. After dispensing of the dose and when the second component returns into the initial configuration, the at least first gasket is repeatedly brought in engagement with both, the housing and the second component.

According to a further example the second component is rotatable relative to the first component during at least one of setting of the dose and dispensing of the dose. The degree of rotation of the second component relative to the first component is directly correlated to the size of the dose actually set or dispensed. With some examples, the second component is rotatable relative to the housing during at least one of setting of the dose and dispensing of the dose. With some examples, the second component is subject to a dose incrementing rotation relative to the housing and/or relative to the first component as a dose size is increased through dialing of the second component along the dose incrementing direction.

With some examples the second component is rotatable relative to the housing during and/or for dispensing of the dose. It may be then non-rotatable to the housing and hence rotationally fixed to the housing for setting of the dose or during setting of the dose.

During dispensing of the dose, the second component may be subject to a rotation along an opposite, hence along a second direction, hence along a dose decrementing direction. The rotation of the second component along the first or dose incrementing direction may be accompanied by a sequence of increasing consecutive numbers appearing in the dosage window of the housing. During dose dispensing and when the second component is subject to a rotation along the second, hence dose decrementing direction, the numbers illustrated in the dosage window appear in a decreasing order.

Since the first and the second component are rotatable relative to each other during at least one of dose setting and dose dispensing the electronic detector provided and fastened to one of the first component and the second component and interacting with the code provided on the other one of the first component and the second component is able to quantitatively measure the degree of relative rotation between the first component and the second component. In this way, a relative rotation between the first component and the second component can be precisely determined and/or measured.

According to another example the code as provided on one of the first component and the second component comprises a rotary encoding. The code may comprise a grey code, e.g. a circular or rotary pattern of distinguishable code sections. The code sections may distinguish with regard to their magnetic, optical, visual, electrostatic, capacitive, acoustic or electrically inductive properties. The type of distinguishing code section is directly correlated to the sensitivity of the electronic sensor. Typically, the rotary encoding may comprise a circular structure on one of the first component and the second component while the electronic sensor is located axially or longitudinally adjacent to the rotary encoding.

Typically, the electronic sensor is longitudinally aligned to the rotary encoding. As seen in longitudinal direction, the electronic sensor may overlap with the position of the rotary encoding.

With other examples, the rotary encoding is positioned radially offset from the electronic detector or electronic sensor. Then, the electronic sensor and the rotary encoding may be located in a common longitudinal plane or axial plane, e.g. extending perpendicular to the longitudinal direction of the housing.

The rotary encoding may comprise a grey scale encoding. The rotary encoding may be implemented as an absolute encoding or as a relative encoding. With some examples, the rotary encoding may comprise only two different code sections arranged alternately and adjacently along the circumference of the rotary encoding. Depending on the number of code sections the electronic sensor will be implemented to detect a degree of rotation matching with the circumferential size of a single code section.

For instance, if the rotary encoding comprises 24 code sections equidistantly arranged in an alternating order along the circumference of the rotary encoding, the angular resolution of the electronic detector will be about 15°. Hence, every 15° of rotation the electronic sensor interacts with a different distinguishable code section of the rotary encoding. The more distinguishable code sections will be provided on the rotary encoding the higher will be the angular resolution of the electronic detector.

With some examples the electronic detector may comprise at least two electronic sensors located at different circumferential positions with respect to the rotary encoding. With such examples, both electronic sensors may interact with one and the same rotary encoding. In this way, the spatial resolution of the electronic detector and/or the position of the electronic detector can be increased. It is also conceivable, that there are provided numerous rotary encodings on one of the first and second components interacting with numerous electronic sensors provided on the other one of the first and second components of the injection device.

According to another example the first component is movable relative to the second component along the longitudinal direction into the trigger position for dispensing of the dose of the medicament. With some examples the first component may be also movable relative to the housing along the longitudinal direction into the trigger position for dispensing of the dose of the medicament. Typically, the trigger position is located distally offset from the initial position of the first component. In other words, the initial position of the first component is a most proximal position of the first component relative to the second component and/or relative to the housing of the injection device.

With some other examples, the first component is movable relative to the housing and/or relative to the second component towards a proximal longitudinal direction from the initial position towards and into the trigger position. Here, and when arriving at the trigger position the first component can be depressed in distal direction for dispensing of the dose. Movement from the initial position into the trigger position may then occur during setting of the dose.

With some examples, the first component may be subject to a longitudinal movement with regards to both, the second component and to the housing, e.g. during a user-induced dispensing action of the injection device. With some examples, the first component may be biased relative to the second component and/or relative to the housing by a return element. The return element may be implemented as a spring or may comprise a spring mechanically engaged with the first component and mechanically engaged with at least one of the second component and the housing of the injection device.

The return element, hence the spring may be implemented as a so-called trigger spring serving to move the first component into the initial position per default, e.g. when the first component is not depressed, e.g. by a thumb of a user.

With some examples and wherein the second component may comprise or may be implemented in or on a dial extension of the injection device the initial position of the first component may be defined by a relative position to the second component. Here, during setting of a dose, both, the second component and the first component may be subject to a common longitudinal displacement, e.g. in the proximal direction relative to the housing. During such a dose setting displacement the first component may remain in the initial position relative to the second component. A movement of the first component from the initial position into the trigger position may be obtained through a distally directed longitudinal displacement or movement of the first component relative to the second component. During this movement the second component may be stationary with regard to the housing or may be subject to a distally directed displacement relative to the housing.

According to a further example of the injection device the at least first gasket is sealingly engaged with at least two of the housing, the first component and the second component when the first component is in the initial position. This example may include that the first gasket is sealingly engaged with the first component and with the second component when the first component is in the initial position. By shifting or moving the first component into the trigger position the sealing engagement between the first and the second component may be abrogated. This may also facilitate a movement of the second component relative to the first component, in particular in the course of dose dispensing. Here, the first component may be rotationally locked to the housing or the first component may be for example in frictional engagement with a finger of a users hand while the second component is subject to a rotation relative to the first component and relative to the housing.

During dose dispensing, the first component and the second component may be subject to a longitudinal displacement relative to the housing. For instance, the first component may be constantly or permanently depressed in distal direction and may be urged against the action of a return element into the trigger position relative to the second component or relative to the housing. During dispensing of the dose, the first component may be kept in the trigger position, hence in a depressed position relative to the first component while both, the first and second component are subject to a combined or common longitudinal displacement relative to the housing in distal direction.

With other examples, the second component may remain stationary relative to the housing during dose dispensing. During and/or for dispensing of the dose the first component may have to be moved into the trigger position and has to be kept in the trigger position. For interrupting dispensing of the dose or at the end of dose dispensing the user may simply release the first component, which under the influence of the return element is urged or automatically moved into the initial position. The movement of the first component into the initial position, either relative to the housing or relative to the second component re-engages the sealing between the first component and the second component through the at least first gasket.

Here, the at least first gasket also provides a twofold function. It serves to seal the cavity formed or constituted by at least one of the first component, the second component and the housing. As long as the gasket is engaged with at least two of the first component, the second component and the housing it also serves to provide a kind of a frictional engagement between the respective components. In this way the first gasket also provides a kind of a frictional engagement or a kind of a friction clutch between the respective components of the injection device.

With another example the second component is longitudinally or axially locked to the housing. The second component may be purely rotationally displaceable relative to the housing, typically with the housing long axis as an axis of rotation. Here, the first component is movable in longitudinal direction between the initial position and the trigger position relative to both, the housing and the second component. As the first component is moved in longitudinal direction relative to the housing it is moved equally relative to the second component. This configuration particularly applies for injection devices, wherein the second component, e.g. in form of a dose dial is longitudinally locked to the housing and cannot be moved in longitudinal direction relative to the housing. Such injection devices may be typically equipped with a mechanical energy reservoir, such as a torsion spring operable to provide the driving force necessary for the drive mechanism to dispense the dose of the medicament from the cartridge, e.g. by providing a respective torque and/or a longitudinally directed thrust or pressure onto a piston rod in operable engagement with a piston of the cartridge.

The above-mentioned examples may also include a configuration, wherein the at least the first gasket is sealingly engageable with the housing and with one of the first component and the second component. This may particularly apply for configurations, wherein the cavity is formed by at least one of the first component and the second component and wherein this cavity is sealed by the housing, in particular when the first component and/or the second component are in an initial position or in a zero dose configuration, i.e. before setting of a dose or after dispensing of a dose.

Setting of a dose may be accompanied or may come along with a longitudinal displacement of the second component by way of which the housing or body of the injection device is separated in longitudinal direction from any one of the first component and the second component. Here, the sealing engagement between the housing and at least one of the first component and the second component is abrogated at the beginning of dose setting. During setting of the dose, the sealing engagement may remain abrogated. The same may apply during dispensing of the dose. A sealing engagement of the at least first gasket with the housing and with at least one of the first component and the second component may take place at the end of dose dispensing, i.e. when the injection device or drive mechanism reaches the zero dose configuration.

Generally, and as long as the first component is in the initial position relative to the second component the at least first gasket serves to provide a frictional engagement between the first component and the second component. The first component may be rotationally locked to the housing. The second component may be subject to a dialing motion or to a rotation for setting of a dose. During dose setting, the first component may remain stationary relative to the housing. With some examples, the first component may also be rotated in unison with the second component. However, during dispensing of the dose, the first component is typically depressed in longitudinal distal direction by a thumb of a user, thereby bringing the first component into the trigger position relative to the second component.

As a consequence, a clutch of the drive mechanism is switched and the drive mechanism is set into a dispensing mode. Longitudinal displacement of the first component relative to the second component also abrogates the sealing engagement between the first component and the second component through a longitudinally directed displacement of the gasket relative to one of the first component and the second component. By abrogating the sealing engagement between the first component and the second component the second component is allowed to rotate relative to the first component at a reduced degree of friction compared to a configuration, in which the first component and the second component are sealingly engaged by the at least first gasket.

According to another example the at least first gasket is fastened to one of the housing, the first component and the second component. The at least first gasket is disengaged from the other two of the housing, the first component and the second component when the first component is in the trigger position. Typically, the at least first gasket is sealingly engaged with at least one of the other two of the housing, the first component and the second component when the first component is in the initial position. In this way, the cavity is effectively sealed against ingress of impurities, at least as long as the first component is in the initial position. Displacing or moving of the first component into the trigger position may then abrogate the sealing engagement between the housing, the first component or second component with the other two of the housing, the first component and the second component.

When for instance the first gasket is fastened to or fixed to the first component it may be sealingly engaged with the housing and/or with the second component as long as the first component is in the initial position. Moving of the first component into the trigger position relative to the housing and/or relative to the second component is accompanied by a respective movement of the first gasket relative to the second component and/or relative to the housing. This longitudinal combined displacement of the first component and the gasket leads to an abrogation of the sealing engagement between the at least first gasket and at least one of the second component and the housing.

With other examples and wherein the first gasket is fastened to the second component or to the housing it is in sealing engagement with the first component as long as the first component is in the initial position relative to the second component or relative to the housing. Moving of the first component into the trigger position relative to at least one of the second component and the housing then at least temporally abrogates the sealing engagement between the housing and at least one of the first component and the second component. The sealing engagement may be already abrogated when the second component is moved relative to the housing, e.g. in the course of setting of a dose, which may be accompanied by a longitudinal displacement of both, the first and the second component relative to the housing in proximal direction.

According to a further example the injection device comprises at least a second gasket. When the first gasket is fastened or attached to one of the housing, the first component and the second component the at least second gasket is fastened to another one of the housing, the first component and the second component. In other words, the at least second gasket is fastened to that one of the housing, the first component and the second component which is not provided with the first gasket. Typically, the first gasket and the second gasket are mutually engaged when the first component is in the initial position. The first gasket and the second gasket are disengaged from each other when the first component is in the trigger position.

With some examples, the first gasket is attached and/or fixed to the first component. The second gasket is attached and/or fixed to the second component. In the initial position of the first component, the first gasket and the second gasket are mechanically engaged. The first gasket and the second gasket may be in longitudinal or radial abutment with regard to the elongation of the housing. By shifting or moving the first component into the trigger position, the mutual engagement of the first gasket and the second gasket is abrogated. In this way, the sealing provided by the mutual engagement of the first gasket and the second gasket is at least temporally abrogated and the first component may be mechanically decoupled from the second component. This may facilitate dispensing of the dose, which may be accompanied by a rotation of the second component relative to the housing and/or relative to the first component.

According to another example the at least first gasket is provided on one of a proximal end face of the housing and a longitudinal end face of one of the first component and the second component. The longitudinal end face may be implemented as a proximal end face or as a distal end face. When provided by the first component, the longitudinal end face typically implemented as a distal end face to engage with the proximal end face of the housing. When provided by the second component, the longitudinal end face is typically implemented as a distal end face to engage with the proximal end face of the housing or it is implemented as a proximal end face to engage with the first component. The at least first gasket is sealingly engaged with the proximal end face and the distal end face when the first component is in the initial position. The same may apply, when the second component is in the initial position. Here, the at least first gasket may be arranged in an axial or longitudinal gap between the proximal end face of the housing and a distal end face of at least one of the first component and the second component.

The proximal end face may be located at a proximal longitudinal end of the housing. With some examples, the proximal end face is located distally from the proximal end of the housing but faces in proximal direction. The same may apply to the distal end face of at least one of the first component and the second component. The distal end face may be provided at a respective distal end of at least one of the first component and the second component. With some examples, the distal end face may be located proximally from a distal end of the respective first or second component. In this case, the distal end face faces in distal direction and is configured to sealingly engage or abut with the proximal end face. Here, the at least first gasket is arranged between the distal end face and the proximal end face. The at least first gasket may seal a gap between the distal end face and the proximal end face.

According to another example the first component comprises a first sidewall and the second component comprises a second side wall. The second sidewall at least partially surrounds the first sidewall. The at least first gasket is fastened to one of the first sidewall and the second sidewall.

At least the first gasket is facing towards the other one of the first sidewall and the second sidewall. With some examples, the first sidewall is of tubular shape. The second sidewall is also of tubular shape. The second sidewall may entirely enclose the first sidewall. The first component and the second component may be arranged in a nested or convoluted way as seen in longitudinal direction. The first sidewall may be in a sliding engagement with the second sidewall. For instance, the first component may be slidably supported in, on or by the second component. Here, an outside surface of the first sidewall may be in sliding engagement with an inside surface of the second sidewall. In this way, the first component may be longitudinally guided in or by the second component.

By arranging the at least first gasket between the first sidewall and the second sidewall, a gap between the first sidewall and the second sidewall can be effectively closed or sealed. With some examples, the at least first gasket is fixed or fastened to an outside surface of the first sidewall. When the first component is in the initial position the at least first gasket is in sealing engagement with an inside surface of the second sidewall. By moving the first component relative to the second component in longitudinal direction and by shifting the first component into the trigger position the at least first gasket is moved relative to the second sidewall in such a way, and that the at least first gasket is effectively disengaged from the second sidewall. This may be achieved by moving of the first gasket into a longitudinal section or region of the second sidewall featuring an enlarged inner diameter.

This may be also achieved by moving of the at least first gasket simply out of engagement with the second sidewall, e.g. by shifting the at least first gasket beyond a longitudinal end of the second sidewall.

With some examples, at least one of the first component and the second component comprises a cup-shaped receptacle which is effectively closed by the other one of the first component and the second component. The cup-shaped receptacle of at least one of the first component and the second component may effectively provide the cavity to receive or to accommodate the electronic detector and the corresponding code. With some examples, both, the first component and the second component each comprise a cup-shaped receptacle. For instance, the receptacle of the second component is open towards the proximal direction. The cup-shaped receptacle of the first component is open towards the distal direction. Here, both, the first component and the second component may complement each other to form the cavity for the electronic detector and the corresponding code.

According to a further example the at least first gasket is attached to one of the first sidewall and the second sidewall. The first gasket is protruding from the respective side wall towards the other one of the first sidewall and the second sidewall. With some examples and when the at least first gasket is attached to e.g. an outside surface of the first sidewall it may protrude from the first sidewall radially outwardly. It may be then in engagement with an inside surface of the second sidewall. It may protrude towards the second sidewall. The same or the like configuration may be provided with the at least first gasket being attached to the second sidewall. Here, it may be attached or fixed to an inside surface of the second sidewall and may protrude radially inwardly towards the first sidewall. A radially inner end of the gasket may be in engagement with an outside surface of the first sidewall.

Here it is also conceivable, that the at least first gasket is attached to the first sidewall and that the at least second gasket is attached to the second sidewall. With the first component being in the initial position the first and the second gasket may be in axial or longitudinal engagement. By moving or shifting the first component into the trigger position, the first and second gasket may be separated from each other along the longitudinal direction. They may be separated in the longitudinal direction, thereby abrogating the sealing engagement between the first and second gaskets and hence between the first and the second sidewall of the first component and the second component, respectively.

According to a further example at least one of the first sidewall and the second sidewall comprises at least one of a tapering section, a curved section and a bulged section as seen in longitudinal direction. Apart from a tapering section, a curved section and a bulged section the first sidewall and/or the second sidewall may comprise a somewhat tubular or cylindrical shape. By providing a tapering section, a curved section or a bulge section on at least one of the first sidewall and the second sidewall a radial gap between the respective sidewall and a gasket attached to the other one of the first or second sidewall can be modified through a longitudinal mutual displacement of the first component and the second component.

With some examples, the at least first gasket provided on one of the first sidewall and the second sidewall may be in sealing engagement with a bulged or protruding section of the other one of the first sidewall and the second sidewall when the first component is in the initial position. By displacing the first component into the trigger position, this engagement may be abrogated since the bulged or protruding section is subject to a longitudinal displacement relative to the gasket. The same may apply to an outwardly curved section or a tapering section of at least one of the first sidewall and the second sidewall.

It is generally sufficient, when only one of the first sidewall and the second sidewall comprises a radially protruding portion or radially recessed portion, e.g. in form of a tapering section, a curved section or a bulged section whereas the other one of the first sidewall and the second sidewall is of rather straight or evenly-shaped geometry in longitudinal direction.

According to another example the at least first gasket is in sealing engagement with the first sidewall and with the second sidewall when the first component is in the initial position. In this way, the cavity provided in or formed by the first and the second components is effectively sealed and protected against ingress of impurities.

According to a further example the at least first gasket is sealingly disengaged from at least one of the first sidewall and the second sidewall when the first component is in the trigger position. Here, the trigger position is defined by a specific position of the first component relative to the second component. In this way, the sealing engagement provided by the at least first gasket between the first sidewall and the second sidewall can be effectively abrogated. As a consequence, the second sidewall and hence the second component may be freely rotatable relative to the first component during dispensing of the dose.

According to a further example the first component comprises a trigger or a trigger button provided at a proximal end of the injection device. The trigger is typically depressible in longitudinal distal direction for dispensing of the dose. Typically, the trigger is in axial engagement or is permanently connected to a clutch of the drive mechanism of the injection device. By depressing the trigger and hence the first component in distal direction relative to the housing and/or relative to the second component the clutch of the drive mechanism is switched into a dispensing mode, in which a user-induced and distally directed force applied to the trigger or dial extension of the injection device is transferred or transmitted into a respective distally directed displacement of a piston rod thereby moving a piston of the cartridge relative to a barrel of the cartridge in distal direction, thus leading to the dispensing of a dose in accordance to the longitudinal advancing motion of the piston rod relative to the barrel of the cartridge.

With other implementations of the drive mechanism and by switching of the drive mechanism into a dispensing mode, mechanical energy stored in the drive mechanism, e.g. mechanical energy stored in a torsion spring is released in order to advance the piston rod in distal direction accordingly.

According to another example the second component comprises one of a dose dial and a dial extension. The second component is rotatable relative to the housing for setting of the dose of the medicament. Depending on the specific implementation of the drive mechanism the dose dial may be fixed in longitudinal direction to the housing and may be exclusively rotationally supported on the housing. By rotating the dial extension e.g. clockwise relative to the housing a size of a dose can be increased. By rotating the dial extension in the opposite direction, e.g. counter-clockwise a size of a dose can be decreased. During dose dispensing the dose dial may rotate in a dose decrementing direction. With some examples, the dose dial may be stationary relative to the housing during dose dispensing.

When the second component is implemented as a dial extension it is typically subject to a proximally directed longitudinal displacement relative to the housing during setting of a dose. It is then subject to a distally directed longitudinal displacement relative to the housing during dispensing of the dose. When implemented as a dial extension the trigger is typically supported on the dial extension and is hence also subject to a respective longitudinal displacement during both, dose setting and dose dispensing. However, for switching of the drive mechanism from the default dose setting mode into the dose dispensing mode the trigger or trigger button is subject to a dedicated distally directed displacement or a distally directed sliding motion relative to the second component, hence relative to the dial extension.

According to another example the injection device is equipped with a cartridge filled with the medicament. The cartridge typically comprises a tubular-shaped barrel sealed in proximal direction by a bung. The bung is typically movable inside the barrel along the longitudinal direction of the barrel. A distal end of the barrel or cartridge is typically sealed by a pierceable seal, e.g. by a septum penetrable by a double-tipped injection needle.

The cartridge may be readily arranged inside the housing of the injection device. The injection device may be implemented as a disposable injection device, wherein the cartridge is prefilled and is assembled inside the housing when commercially distributed or handed out to end users or patients.

With other examples, the injection device is a reusable injection device. Here, the cartridge may be replaceably arranged inside the housing.

The at least first gasket and/or the at least second gasket may comprise an annular structure. It may be provided as a kind of an O-ring. The first gasket or second gasket may comprise an elastic material, such as a polymeric or elastomeric material. The gasket may comprise for instance an epoxy resin or silicone or mixtures thereof. The first or second gaskets may be also provided by a coating on at least one of the housing, the first component and the second component. The first or second gaskets may be attached to the first component, second component of the housing by means of a hot melt procedure, injection molding or insert molding. The first and/or the second gasket may comprise a foamed material, such a foamed plastic, a foamed rubber, a foamed thermoplastic material. The first and/or the second gasket may comprise a thermosetting material.

The first and/or the second gasket may be unitarily formed. They may be provided as a single piece. With some examples the first and/or the second gasket may each comprise a multi-component gasket featuring at least a first and a second section. The first and/or the second gasket may comprise a multi-component clamp or bracket to wrap around a sidewall of the first or second component, respectively.

The first or second gasket may be extruded onto at least one of the housing, the first component and the second component. Comparatively soft or elastic materials used for the first or second gaskets provide an effective sealing of the cavity. The first and/or the second gasket may be adhesively or cohesively attached to at least one of the housing, the first component and the second component.

With some further examples the electronic detector comprises a printed circuit board provided with a processor, a battery and an electronic sensor. With some examples, the printed circuit board of the electronic sensor may get in sealing engagement with at least one of the first gasket and the second gasket when the first component is in the initial position. The sealing engagement between the printed circuit board and the respective gasket may be abrogated by moving of the first component relative to at least one of the housing and the second component.

Generally, the scope of the present disclosure is defined by the content of the claims. The injection device is not limited to specific embodiments or examples but comprises any combination of elements of different embodiments or examples. Insofar, the present disclosure covers any combination of claims and any technically feasible combination of the features disclosed in connection with different examples or embodiments.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

It will be further apparent to those skilled in the art that various modifications and variations can be made to the present disclosure without departing from the scope of the disclosure. Further, it is to be noted, that any reference numerals used in the appended claims are not to be construed as limiting the scope of the disclosure.

BRIEF DESCRIPTION OF THE FIGURES

In the following, numerous examples of the injection device and the method of pairing a data logging device with an external electronic device will be described in greater detail by making reference to the drawings, in which.

DETAILED DESCRIPTION

Figures 1, 2:
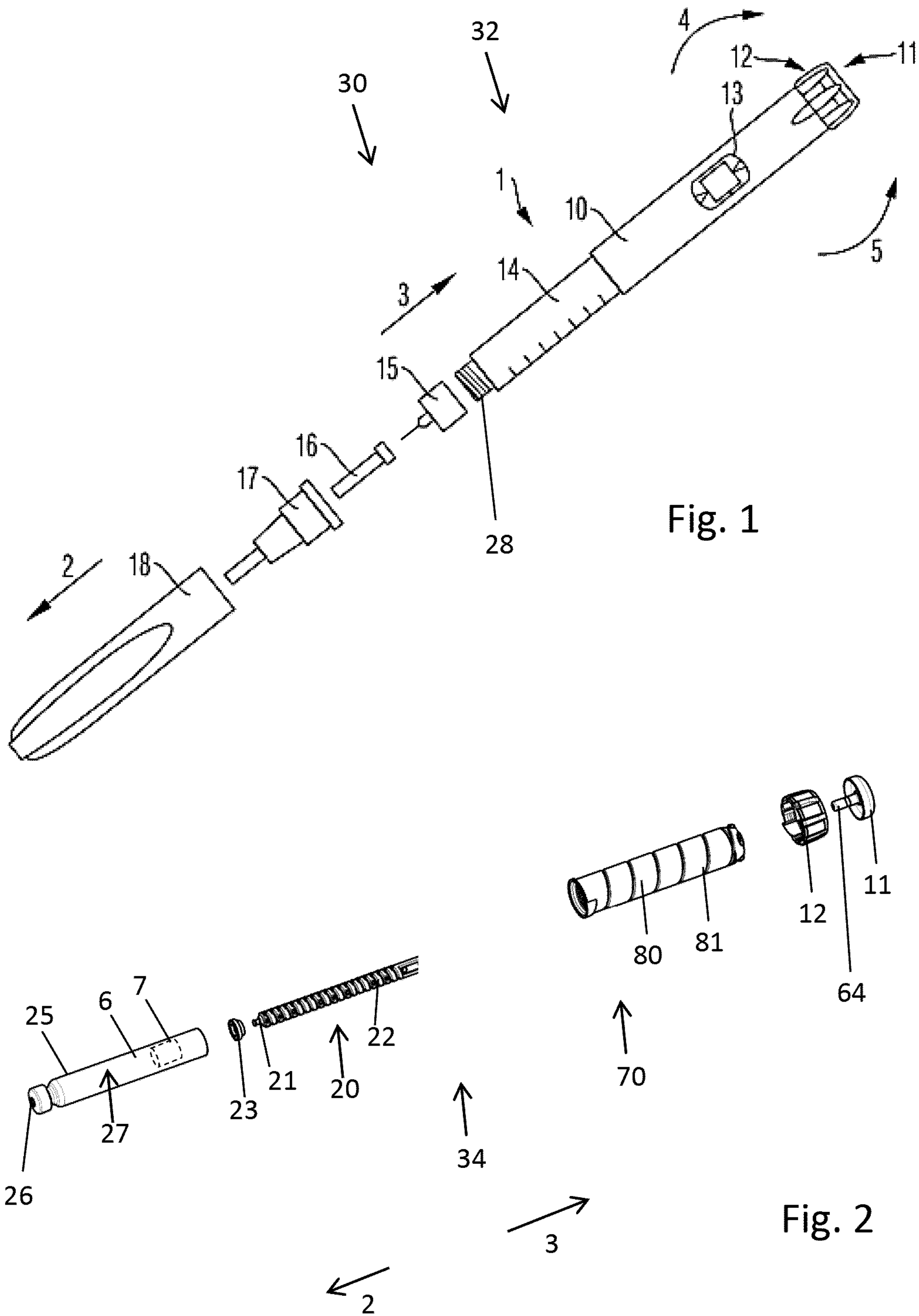
FIG. 1 schematically illustrates an example of a drug delivery device implemented as an injection device, FIG. 2 schematically illustrates numerous components of the drug delivery device of FIG. 1.

One example of a drug delivery device 1 for administering of a dose of a medicament 27 is illustrated in FIGS. 1 and 2. The drug delivery device 1 is implemented as an injection device 30.

The injection device 30 is a handheld pen-type injector. The injection device 30 may be implemented as a disposable injection device 30. It may comprise a pre-filled cartridge 6 arranged inside a cartridge holder 14. With a disposable injection device 30, the cartridge holder 14 may be non-detachably connected to a body 10 of a housing 32 of the injection device 30.

With other examples, the injection device 30 is a re-usable injection device, wherein the cartridge holder 14 is detachably connected to the body 10 for replacing an empty cartridge 6. At or near a distal end of the housing 32, hence at the distal end of the cartridge holder 14, there is provided a socket 28 configured to mount or to engage with an injection needle 15. The socket 28 may be implemented as a threaded socket and the injection needle 15 may comprise a needle hub begin correspondingly threaded to provide a threaded engagement with the socket 28.

Typically, the injection needle 15 is protected by an inner needle cap 16 and either by an outer needle cap 17 and/or a protective cap 18 that is configured to enclose and to protect a distal section of the housing 32 of the injection device 30. The body 10 may comprise and form a main housing part configured to accommodate a drive mechanism 34 as shown in FIG. 2. The cartridge holder 14 may be regarded as a distal housing component of the injection device 30. The cartridge holder 14 may be permanently or releasably connected to the body 10 or main housing.

The cartridge 6 comprises a cylindrically-shaped or tubular-shaped barrel 25 sealed in proximal direction 3 by a bung 7 located inside the barrel 25. The cartridge six may be prefilled with a liquid medicament 27. The bung 7 is displaceable relative to the barrel 25 of the cartridge 6 in a distal direction 2 by means of a piston rod 20 of the drive mechanism 34. A distal end of the cartridge 6 is sealed by a pierceable seal 26 configured as a septum and being pierceable by a proximally directed tipped end of the injection needle 15. By attaching the injection needle 15 to the distal end of the cartridge holder 14 the seal 26 of the cartridge 6 is penetrated thereby establishing a fluid transferring access to the interior of the cartridge 6.

When the injection device 1 is configured to administer e.g. human insulin, the dosage set by a dose dial 12 at a proximal end of the injection device 1 may be displayed in so-called international units (IU, wherein 1 IU is the biological equivalent of about 45.5 μg of pure crystalline insulin (1/22 mg). The dose dial 12 may comprise a sleeve shaped knob at the proximal end of the housing 32 of the injection device 30.

As shown further in FIGS. 1 and 2, the body 10 comprises a dosage window 13 that may be in the form of an aperture in the body 10. The dosage window 13 permits a user to view a limited portion of a number sleeve 80 that is configured to move when the dose dial 12 is turned. The number sleeve 80 and the dosage window 13 provide a visual indication of a dose currently set. The dose dial 12 may be rotated on a helical path with respect to the body 10 when turned during setting and/or dispensing or expelling of a dose.

The injection device 30 may be configured so that turning the dosage knob 12 causes a mechanical click sound to provide acoustical feedback to a user. The number sleeve 80 mechanically interacts with a piston in the insulin cartridge 6. When the needle 15 is stuck into a skin portion of a patient, and when the trigger 11 or injection button is pushed, the insulin dose displayed in the dosage window 13 will be ejected from injection device 1. When the needle 15 of the injection device 1 remains for a certain time in the skin portion after the trigger 11 is pushed, a high percentage of the dose is actually injected into the patient's body. Ejection of an insulin dose may also cause a mechanical click sound, which is however different from the sounds produced when using the dose dial 12.

In the illustrated embodiment, during delivery of the insulin dose, the dose dial 12 is turned to its initial position in an axial movement, that is to say without rotation, while the number sleeve 80 is rotated to return to its initial position, e.g. to display a dose of zero units.

The injection device 30 may be used for several injection processes until either the cartridge 6 is empty or the expiration date of the medicament in the injection device 1 (e.g. 28 days after the first use) is reached.

At least some components of an example of a drive mechanism 34 are illustrated in more detail in FIG. 2. The drive mechanism 34 comprises numerous mechanically interacting components. A flange like support of the housing 10 comprises a threaded axial through opening threadedly engaged with a thread 22 of the piston rod 20. The distal end of the piston rod 20 comprises a bearing 21 on which a pressure foot 23 is free to rotate with the longitudinal axis of the piston rod 20 as an axis of rotation. The pressure foot 23 is configured to axially abut against a proximally facing thrust receiving face of the bung 7 of the cartridge 6. During a dispensing action the piston rod 20 rotates relative to the housing 10 thereby experiencing a distally directed advancing motion relative to the housing 10 and hence relative to the barrel 25 of the cartridge 6. As a consequence, the bung 7 of the cartridge 6 is displaced in distal direction 2 by a well-defined distance due to the threaded engagement of the piston rod 20 with the housing 10.

Furthermore, there is provided a dose dial sleeve also denoted as number sleeve 80. The number sleeve 80 is located radially inward of the housing 10. A helical groove 81 is provided about an outer surface of the number sleeve 80. The body 10 is provided with the dosage window 13 through which a part of the outer surface of the number sleeve 80 can be seen. The body 10 is further provided with a helical rib at an inside sidewall portion, which helical rib is to be seated in the helical groove 81 of the number sleeve 80. The helical rib fixed to the body 10. It may be unitarily formed with the body 10. There may be provided first and second stops on the body 10 to limit a dose setting procedure during which the number sleeve 80 is rotated in a helical motion relative to the housing 10.

The dose dial 12 in form of a dose dial grip is disposed about an outer surface of the proximal end of the number sleeve 80. An outer diameter of the dose dial 12 typically corresponds to and matches with the outer diameter of a proximal end of the body 10. The dose dial 12 is secured to the number sleeve 80 to prevent relative movement there between. The dose dial 12 is provided with a central opening.

A trigger 11, also denoted as dose button is substantially T-shaped. It is provided at a proximal end of the injection device 10. A stem 64 of the trigger 11 extends through the opening in the dose dial 12. The stem 64 and hence the trigger 11 is retained for limited axial movement relative to the number sleeve 80. A head of the trigger 11 is generally circular. The trigger side wall or skirt extends from a periphery of the head and is further adapted to be seated in a proximally accessible annular recess of the dose dial 12. Typically, the trigger 11 is in axial or longitudinal engagement with a clutch 90, by way of which the drive mechanism is switchable from a default dose setting mode into a dose dispensing mode. In the dose dispensing mode, the injection device 30 is operable to expel or to dispense a dose of the medicament from the cartridge 6.

To dial a dose a user rotates the dose dial 12, along a dose incrementing direction 4, e.g. clockwise. Dialing of a dose may be accompanied by a clicking sound. In this way, audible and/or tactile feedback of the dose being dialed is provided. Dialing of a dose is further accompanied by a rotation of the number sleeve 80, which starts to extend from the body 10 towards the proximal direction 3 when dialed along a dose incrementing direction 4, e.g. in a clockwise sense.

The number sleeve 80, the dose dial 12 and the trigger may form part of a dial extension 70, hence and assembly of components of the drive mechanism 34 that starts to extend or to displace from the proximal end of the body 10 as a dose is dialed. During dispensing of a dose, hence when a user depresses the trigger 11 in distal direction 2, the dial extension 70 is subject to a distally directed movement relative to the body 10, hence along the distal direction 2. During such a dispensing motion, the number sleeve 80 is subject to a rotation along a dose decrementing direction 5, e.g. counter-clockwise.

The expelling mechanism or drive mechanism 34 as described above is only exemplary for one of a plurality of differently configured drive mechanisms that are generally implementable in a disposable or re-usable pen-injector. The drive mechanism as described above is explained in more detail e.g. in WO2004/078239A1, WO 2004/078240A1 or WO 2004/078241A1 the entirety of which being incorporated herein by reference.

Figure 3:
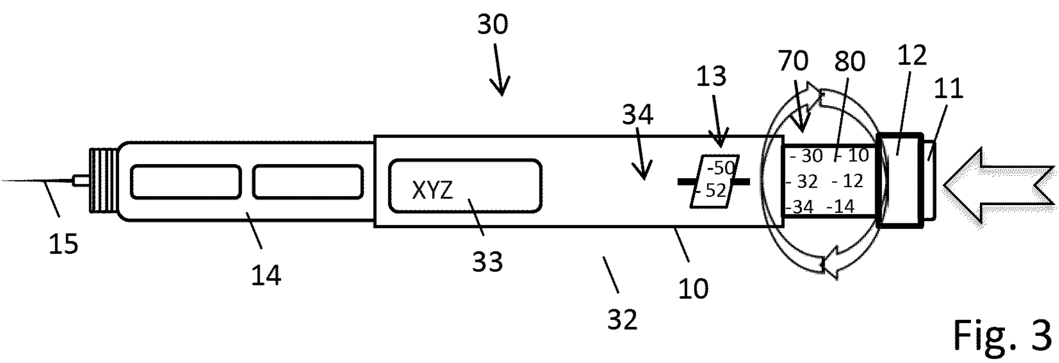
FIG. 3 is illustrative of a pen-type injection device after setting of a dose.

The pen-type injection device 30 as illustrated in FIG. 3 comprises a housing 32 featuring a proximal housing component denoted as body 10 and a distal housing component denoted as cartridge holder 14. The drive mechanism 34, the details of which not being illustrated here in greater detail comprises a dial extension 70. The dial extension 70 is subject to a proximally directed displacement relative to the body 10 in the course of setting of a dose. The dial extension 70 is subject to a distally directed displacement during dispensing of the dose. The dial extension 70 comprises a dose dial 12 rotatable relative to the body 10 for setting of the dose. The size of the dose typically shows up in the dosage window 13. The number sleeve 80 may also contribute or may form part of the dial extension 70. The numbers provided on an outside surface of the number sleeve 80 may be visible on that part of the dial extension 70 protruding proximally from the proximal end of the body 10 when a dose of a particular size has been set.

For dispensing of the dose a user has to depress the injection button 11 provided at the proximal end of the dial extension 70.

Figure 4:
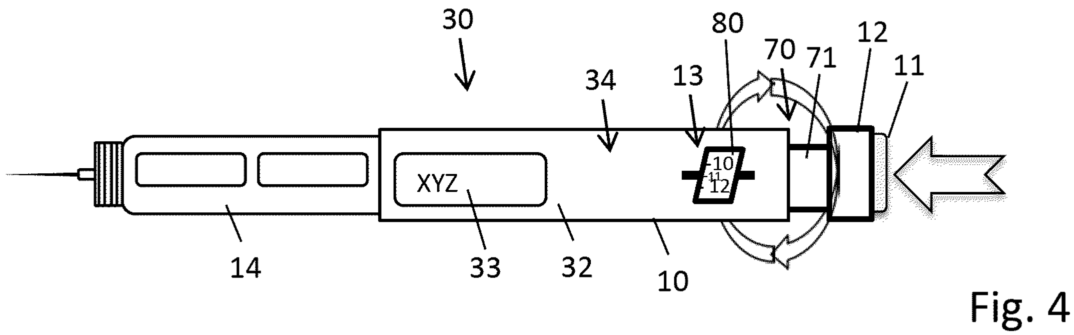
FIG. 4 is illustrative of a further example of a pen-type injection device after setting of a dose and FIG. 5 is illustrative of another example of a pen-type injector after setting of a dose and before dispensing of a dose.

The example of another injection device 30 as illustrated in FIG. 4 is quite similar and hence equivalent to the example as shown in FIG. 3. Here, the dial extension 70 comprises a sleeve 71 that starts to protrude proximally from the body 10 as a dose is set by dialing of the dose dial 12. Also here, the dial extension 70 is subject to a movement in proximal direction 3 when a dose of increasing size is set. During dispensing of the dose, which is initiated by depressing of the trigger 11 in distal direction 2 the dial extension 70 is urged back into the body 10.

With the examples of FIGS. 3 and 4, the driving force leading to a distally directed advancing motion of the piston rod 20 relative to the body 10 and relative to the cartridge 6 is provided by a user urging the dial extension 70 from the dose setting position as illustrated in FIGS. 3 and 4 into the initial configuration, as it is apparent from e.g. FIG. 1.

Figure 5:
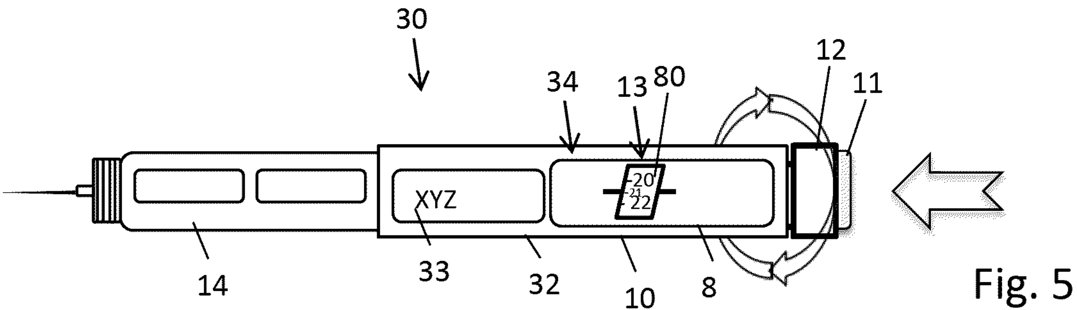

With the further example of an injection device 30 as illustrated in FIG. 5, the driving force for moving of the piston rod 20 in distal direction 2 may be provided by a mechanical energy storage provided inside the body 10. The mechanical energy storage may comprise a torsion spring. An example of such a drive mechanism is shown in WO 2014/033195 A1 the entirety of which being incorporated herein by reference.

Dialing or setting of a dose is obtained through a rotation of the dose dial 12 relative to the body 10. As illustrated in FIG. 5, a dose of a particular size has been set and a respective dose size indicating number shows up in the dosage window 13. The dosage window 13 may be a movable window displaceable in longitudinal direction in a fixed window or aperture 8 provided in the body 10. The movable dosage window 13 may be provided by a gauge element rotationally locked and longitudinally displaceable relative to the body 10. While the number sleeve 80 may be threadedly engaged with the body 10 with the examples of FIGS. 3 and 4 the number sleeve 80 of the example of FIG. 5 may be longitudinally or axially locked to the body 10.

With the examples of numerous injection devices 30 as illustrated in FIG. 3-5 the dose dial 12 serves as a second component 200 that is rotatable relative to the housing 32 relative to the body 10 for at least for one of setting of the dose and dispensing of the dose. The trigger 11 or trigger button is movable relative to the housing 32 or body 10 or relative to the second component 200 for switching of the injection device 30 from a dose setting mode into a dose dispensing mode. Typically, the first component 100 or the trigger 11 is displaceable from a proximal initial position into a distally directed trigger position as it is apparent from a comparison of FIGS. 6 and 7. For this, the first component 100 is biased towards the proximal direction 3 by a return element, e.g. in form of a spring 160.

With some examples of the injection device 30, the second component 200 is subject to a rotation relative to the first component 100 during at least one of setting of the dose and dispensing of the dose. In order to detect and to quantitatively measure the degree of relative rotation between the first component 100 and the second component 200 there is provided an electronic detector 300 in a cavity 150 that is provided by or formed by at least one or both of the first component 100 and the second component 200.

The electronic detector 300 comprises at least one electronic sensor 308, 310 provided or attached to one of the first component 100 and the second component 200. The electronic sensor 308, 310 communicates or interacts with a corresponding code 330 provided on the other one of the first component 100 and the second component 200. In the examples as illustrated in FIGS. 6-15 the electronic detector 300 equipped with at least one electronic sensor 308, 310 is attached to and/or fixed to the first component 100. The code 330, e.g. implemented as a rotary encoding 332 is provided on or fixed to the second component 200.

Figure 6:
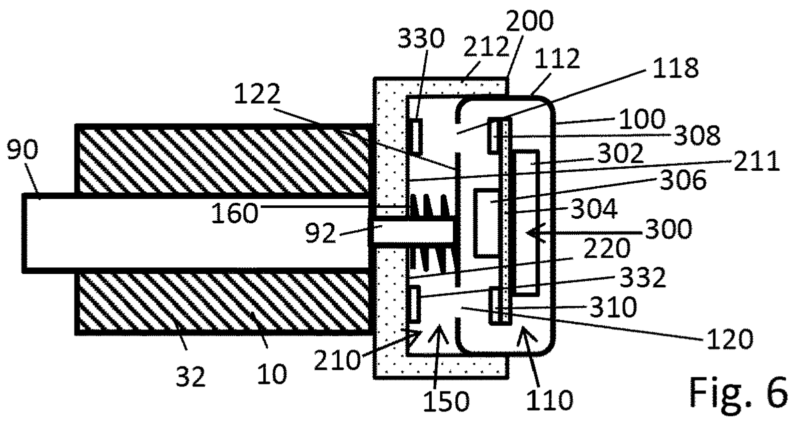
FIG. 6 shows an example of a proximal part of an injection device with first and second components in an initial position.

In the example of FIG. 6 the first component 100 is slidably engaged with the second component 200 along the longitudinal direction. There is provided a spring 160 acting between the first component 100 and the second component 200.

One end of the spring 116, typically implemented as a longitudinally extending compression spring is in longitudinal abutment with a distally facing abutment or abutment face 122 of the first component 100. An opposite end of the spring 160 is in abutment with a proximally facing counter abutment 220 of the second component 200. The counter abutment 220 may be provided in a bottom portion of a cup-shaped receptacle 210 provided or formed by the second component 200.

As illustrated further in FIG. 6, the bottom 211 of the second component 200 is provided with the code 330, e.g. implemented as an annularly-shaped rotary encoding 332. The rotary encoding 332 faces towards the proximal direction 3. The first component 100 comprises a receptacle 110 with a sidewall 112 which is open towards the distal direction 2 whereas the second component 200 comprises a cup-shaped receptacle 210 open towards the proximal direction. The receptacle 210 is confined by a tubular-shaped sidewall 212 that may be in slidable engagement with the complementary shaped tubular sidewall 112 of the first component 100.

In the example as illustrated in FIG. 6, the first component comprises a cup-shaped receptacle 110 confined in proximal direction 3 by a proximal end face 106 and confined by the tubular-shaped sidewall 112. Towards the distal direction 2 the receptacle 110 comprises at least two apertures 118, 120 facing in distal direction and aligned with respective first and second electronic sensors 308, 310 of the electronic detector 300.

As illustrated in FIG. 6, the electronic detector 300 is arranged inside the cup-shaped receptacle 110. It is fixed to the first component 100. The sensors 308, 310 are longitudinally aligned with the apertures 118, 120 of the first component 100. They are facing towards the rotary encoding 332. As the first component 100 is subject to a rotation with regard to the longitudinal axis of the injection device 30 as an axis of rotation there will be a respective rotation of the electronic detector 300 relative to the code 330 and relative to the rotary encoding 332.

Figure 7:
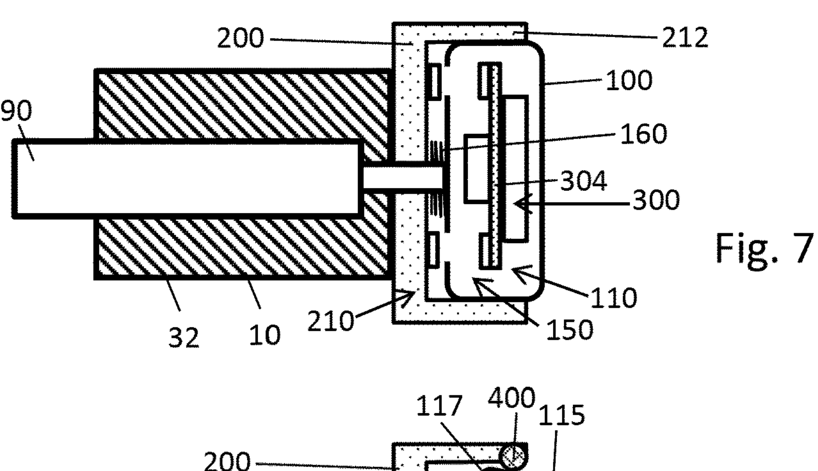
FIG. 7 shows the example of FIG. 6 with the first component in the trigger position.

Since the rotary encoding 332 is encoded in circumferential direction, the respective sensors 308, 310 are operable to detect and to quantitatively measure a degree of rotation of the first component 100 relative to the second components 200. A relative rotation between the first component 100 and the second component 200 may typically arise when the first component 100 is depressed in distal direction 2 relative to the second components 200 as illustrated in FIG. 7. Here, the spring 160 is compressed and the first component 100, in axial or longitudinal abutment with a clutch 90 via an extension 92, serves to displace or to move the clutch 90 relative to the housing 32 or body 10 of the injection device 30, thereby switching the drive mechanism 34 into a dose dispensing mode.

As illustrated in FIGS. 6 and 7, the abutment 122 or bottom portion of the first component 100 is in longitudinal abutment with a longitudinal extension 92 of the clutch 90. By moving the first component 100 from the initial position as illustrated in FIG. 6 into the trigger position as shown in FIG. 7 the clutch 90 is correspondingly moved in distal direction relative to the second component 200 and/or relative to the body 10 or housing 32 of the injection device 30. The movement of the clutch 90 switches the drive mechanism from the default dose setting mode into the dose dispensing mode.

At the same time and due to the longitudinal displacement of the first component 100 relative to the second component 200 or relative to the housing 32 the electronic detector 30 may be activated. Additionally, there may be provided a switch or some other type of activation mechanism for the electronic detector 300 to set the electronic detector into an activated mode. The electronic detector 300 is typically provided with a printed circuit board 304, on which at least the processor 306 and the electronic sensor is 308, 310 are located. The electronic detector 300 is further provided with a battery 302.

Of course, the electronic detector 300 may be further equipped with an electronic storage operable to store the date and/or time of an injection and to store a size of a dose dispensed by the injection device 30. The electronic detector 300 may further comprise a clock generator in order to provide time information for storage of injection-related data in the electronic storage. The electronic detector may be further provided with a communication module, typically implemented as a wireless communication module. The communication module is typically configured and operable to establish a communication link with an external electronic device, such as a smart phone, a tablet computer, a smart watch or some other type of electronic mobile or electronic immobile device. With the communication module, data captured by the electronic detector 300 can be shared with other electronic devices for data analysis.

As it is illustrated in FIGS. 6 and 7, the arrangement of the first component 100 and the second component provides and forms a cavity 150, in which the electronic detector 300 and the corresponding code 330 are located and arranged. Since the first component 100 has to be movable relative to the second components 200, ingress of impurities cannot be entirely avoided due to the requirement that the first component 100 and the second component 200 have to smoothly move relative to each other either during setting of a dose or during dispensing of a dose.

Hence, between the sidewall 212 of the second component and the sidewall 112 of the first component 100 there is always provided a gap of predefined size in order to enable a smooth or relative displacement between the first and the second components 100, 200.

Figure 8:
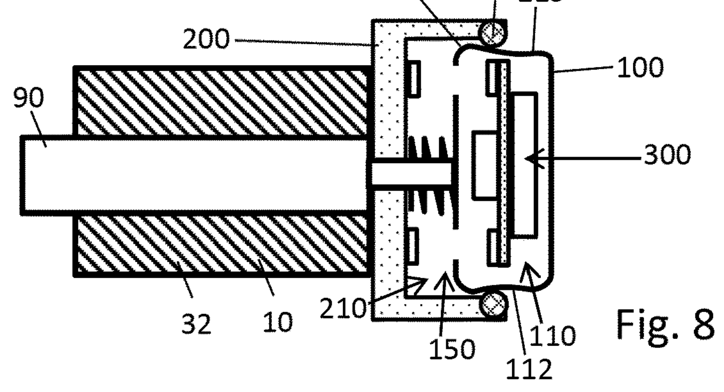
FIG. 8 shows another example of first and second components with the first component in an initial position.
Figure 9:
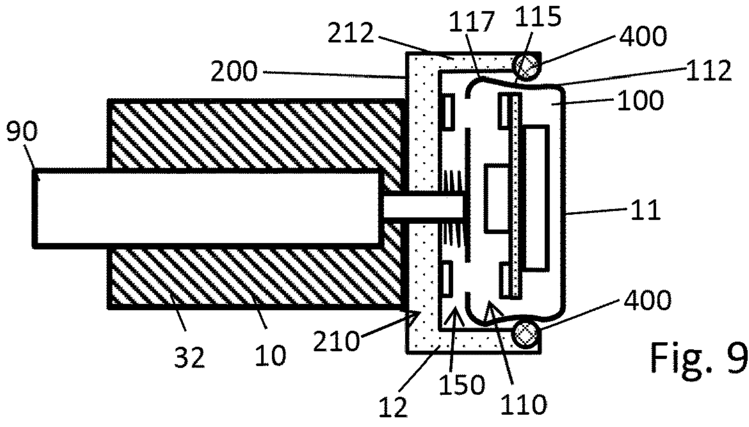
FIG. 9 shows the example of FIG. 8 with the first component in the trigger position.

In the example as illustrated in FIGS. 8 and 9 there is provided at least a first gasket 400 in the interface between the first component 100 and the second component 200. In the configuration of FIG. 8, in which the first component 100 is in the initial position relative to the second components 200 the first component 100, in particular the sidewall 112 of the first component 100 is in sealing engagement with the first gasket 400. Here, the first gasket 400 is attached and fixed to the second component 200. The first gasket 400 is provided at a proximal end of the sidewall 212 of the second component 200.

As it is further apparent from FIGS. 8 and 9 the sidewall 112 of the first component 100 comprises a radially outwardly extending bulged section 117 near its distal end. In the initial position as illustrated in FIG. 8, the outwardly bulged section 117 is in mechanical engagement with the at least first gasket 400. In this way, the cavity 150 formed or provided by the first component 100 and the second component 200 is effectively sealed against ingress of impurities from outside.

As the first component 100 is moved or depressed in distal direction 2 relative to the second component 200 against the action of the return spring 160 as illustrated in FIG. 9 the outwardly bulged portion 170 is displaced distally from the at least first gasket 400. In this way, the bulged portion 117 and the sidewall 112 of the first component 100 is or are decoupled from the first gasket 400. This mechanical decoupling between the sidewall 112 and the gasket 400 allows and supports a smooth and low-friction or even friction-less rotation of the second component 200 relative to the first component 100 in the course of dispensing of a dose.

Even though the disengagement of the sidewall 112 from the gasket 400 temporally abrogates the sealing between the first and the second components 100, 200 it should be noted, that this abrogation of the sealing of the cavity 150 only takes place during a comparatively limited period of time, namely exclusively during dispensing of the dose. At the end of a dose dispensing procedure and when a distally directed thrust, typically exerted by a user onto the first component 100, is no longer present, the spring 160 serves to move and to return the first component 100 into the initial position as illustrated in FIG. 8, in which the sealing between the sidewall 112 and the sidewall 212 is established again.

Figures 10, 11, 12, 13:
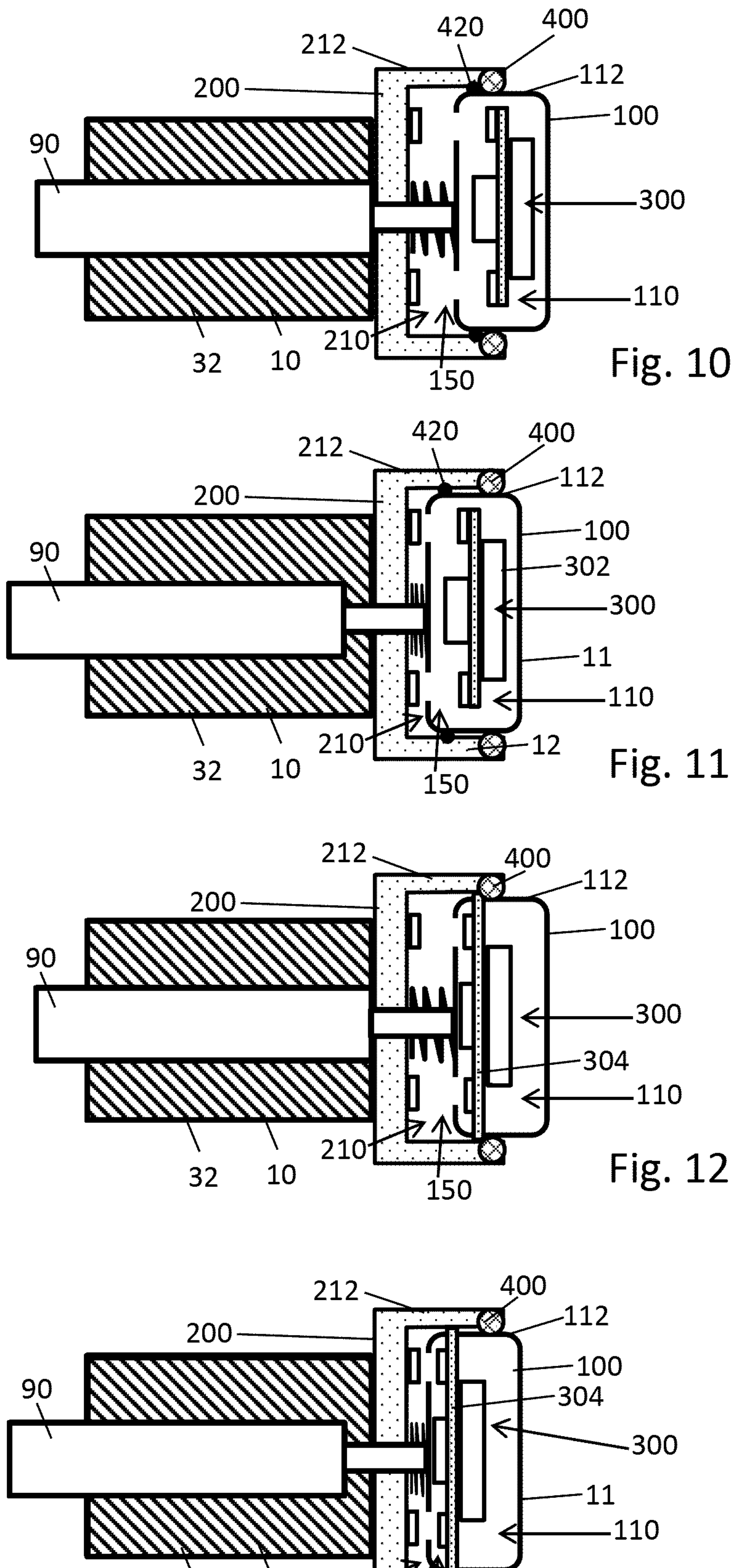
FIG. 10 shows another example of first and second components of an injection device, wherein a cavity between first and second components is sealable by a first gasket and by a second gasket.
FIG. 11 shows the example of FIG. 10 with the first component in the trigger position.
FIG. 12 shows another example of first and second components with the first component in the initial position.
FIG. 13 is illustrative of the example of FIG. 12 with the first component in the trigger position.

In the example of FIGS. 10 and 11 a second gasket 420 is provided in the interface between first and second components 100, 200. Here, the first gasket 400 is attached and fixed to the sidewall 212 of the second component 200. The second gasket 420 is attached and fixed to the sidewall 112 of the first component 100. Since at least a longitudinal portion of the sidewall 112 is entirely enclosed by the second sidewall 212 the second gasket 420 protruding radially outwardly on the sidewall 112 may be in longitudinal or axial abutment or engagement with the first gasket 400 provided on the sidewall 212 of the second component 200. As illustrated in FIGS. 10 and 11, the first gasket 400 is provided at a radially inwardly facing portion of the sidewall 212 and the second gasket 420 is provided on a radially outwardly facing portion of the sidewall 112. In the initial position of the first component 100 relative to the second component 200 the first and the second gaskets 400, 420 are in axial or longitudinal abutment, thereby effectively sealing the cavity 150 as provided or constituted by the cup-shaped receptacle 110, 210 of the first and second components 100, 200, respectively.

Now, as the first component 100 is subject to a distally directed displacement, e.g. a distally directed sliding displacement relative to the second component 200 as illustrated in FIG. 10 the first and second gasket 400, 420 are separated from each other in longitudinal direction. In this way, first and second gaskets 400, 420 are disengaged. This disengagement may be sufficient to allow and to support a rotation of the second component 200 relative to the housing 32 and/or relative to the first component 100.

In the further example of FIGS. 12 and 13 the electronic detector 300, in particular the printed circuit board PCB 304 of the electronic detector 300 at least slightly protrudes from the sidewall 112 radially outwardly. Here, the printed circuit board 304 may also serve as a kind of distal closure for the cup-shaped receptacle 110 of the first component 100. However, the relevant electronic components of the PCB 304, namely the sensors 308, 310 are located on a distally facing side of the PC 304.

With some examples, the PCB 304 may only intersect the sidewall 112 and may protrude radially outwardly from the sidewall 112. In the initial configuration or position of the first component 100 relative to the second component 200 the outwardly protruding portion of the PCB 304 is in sealing engagement with the first gasket 400 provided and fixed on the sidewall 212 of the second component 200. As the first component 100 and the PCB 304 fixed thereto is or are subject to a distally directed displacement as illustrated in FIG. 13, the sealing engagement between the PCB 304 and the first gasket 400 is abrogated. This allows for a rotation of the second component 200 relative to the first component 100 at least during dispensing of the dose.

Figure 14:
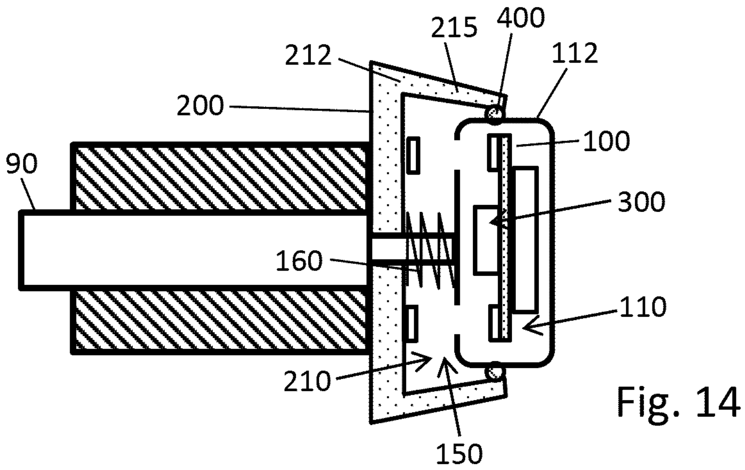
FIG. 14 is another example of first and second components with the first component in the initial position.
Figure 15:
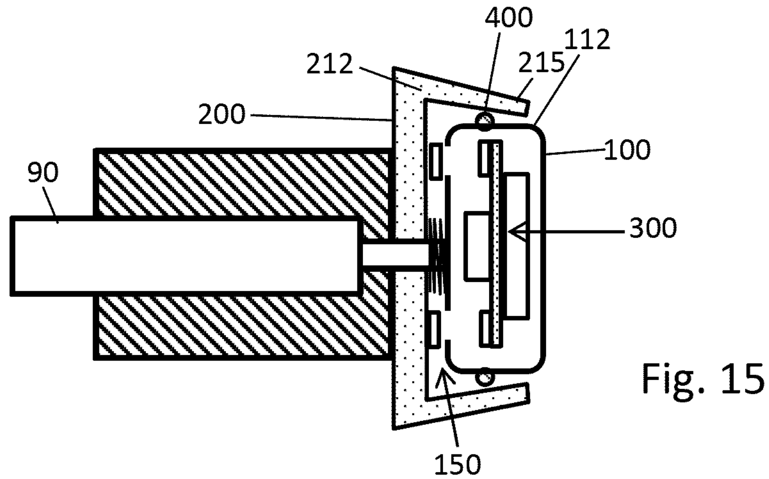
FIG. 15 is illustrative of the example of FIG. 14 with the first component in the trigger position.

In the further example as illustrated in FIGS. 14 and 15 the first gasket 400 is attached and fixed to the first sidewall 112 of the first component 100. Here, the sidewall 212 of the second component 200 comprises a tapering section 215. The tapering section 250 comprises a gradually decreasing inner diameter towards the proximal direction 3. In the initial position of the first component 100 relative to the second component 200 as illustrated in FIG. 14 the first gasket 400 is radially squeezed between an outside surface of the first sidewall 112 and an inside surface of the second sidewall 212. As the first component 100 is subject to a distally directed displacement relative to the second component 200 in distal direction 2 and towards the trigger position as illustrated in FIG. 15 the first gasket 400 starts to slide along the radially widening tapering section 215 of the first sidewall 212. When the trigger position as illustrated in FIG. 15 has been reached, the first gasket 400 may be out of engagement from the second sidewall 212. As a consequence, the second component 200 may freely rotate relative to the housing 32 and/or relative to the first component 100, e.g. during dispensing of the dose.

Figure 16:
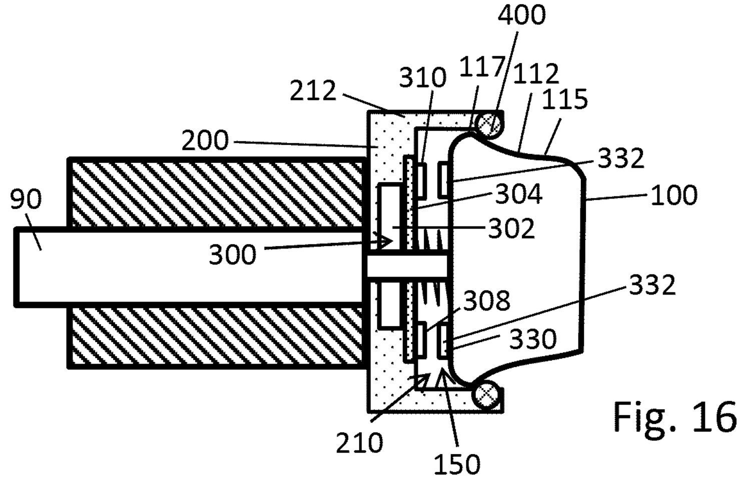
FIG. 16 shows another example of first and second components with the first component in the initial position.
Figure 17:
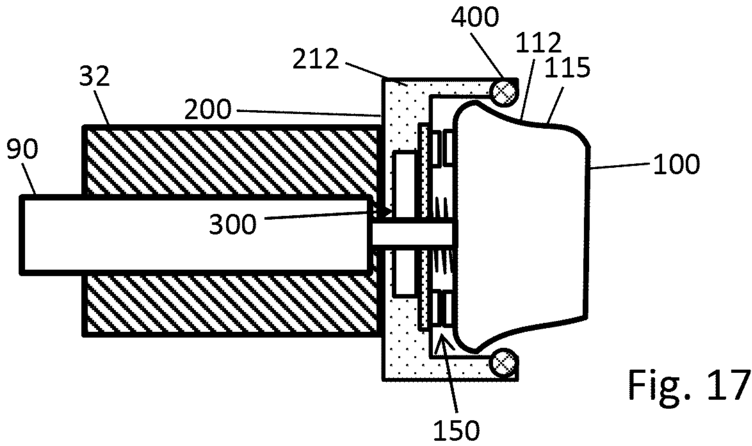
FIG. 17 shows the example of FIG. 16 with the first component in the trigger position.

In the further example as illustrated in FIGS. 16 and 17 the first gasket 400 is again provided at or near a proximal end of the second sidewall 212 of the second component 200. Here, the sidewall 112 of the first component 100 comprises a radially outwardly extending bulged section 117 near a distal end of the first component 100. Proximally adjacent to the bulged section 115 there is provided a radially inwardly extending, e.g. somewhat concave shaped curved section 115. The curved section 115 forms a kind of a radial recess in the outside surface of the first sidewall 112.

In the initial position of the first component 100 as illustrated in FIG. 16 the bulged section 117 is in axial or longitudinal abutment with the first gasket 400. Here, the cavity 150 is effectively sealed against ingress of impurities. As the first component 100 is subject to a distally directed displacement relative to the second components 200 as illustrated in FIG. 17, the radially narrowed or recessed curved section 115 is moved in distal direction 2 and aligns with the first gasket 400. Due to the reduced outside diameter of the curved section 115 compared to the bulged section 117 the sealing engagement between the first gasket 400 and the sidewall 112 of the first component 100 is effectively abrogated. Hence, a smooth rotation of the second component 200 relative to the first component 100 and/or relative to the housing 32 is provided and supported.

In the example of FIGS. 16 and 17 the position of the electronic detector 300 and the code 330 has been switched compared to the numerous examples as described above in connection with FIG. 6-15. Here, the electronic detector 300 is arranged on or inside the second component 200 and the code 330 with the rotary encoding 332 is provided on the first component 100.

Figure 18:
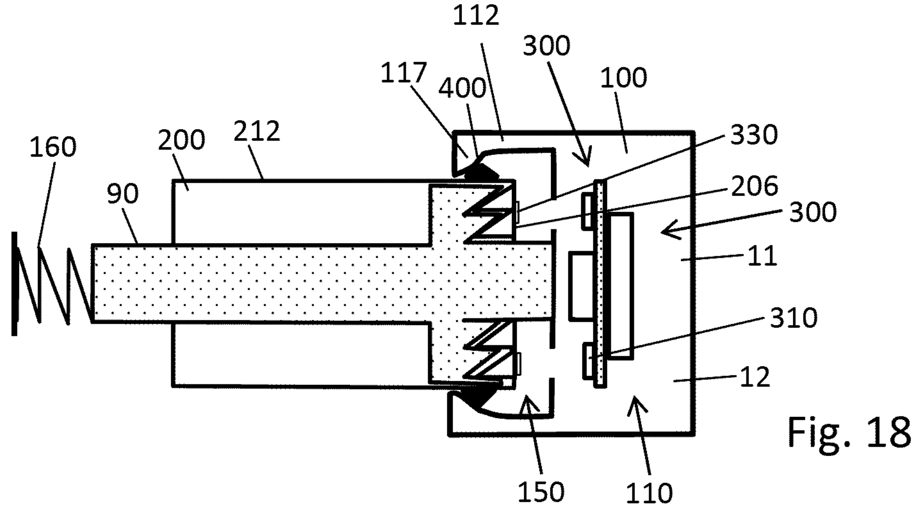
FIG. 18 shows another example of first and second components with the first component in the initial position.
Figure 19:
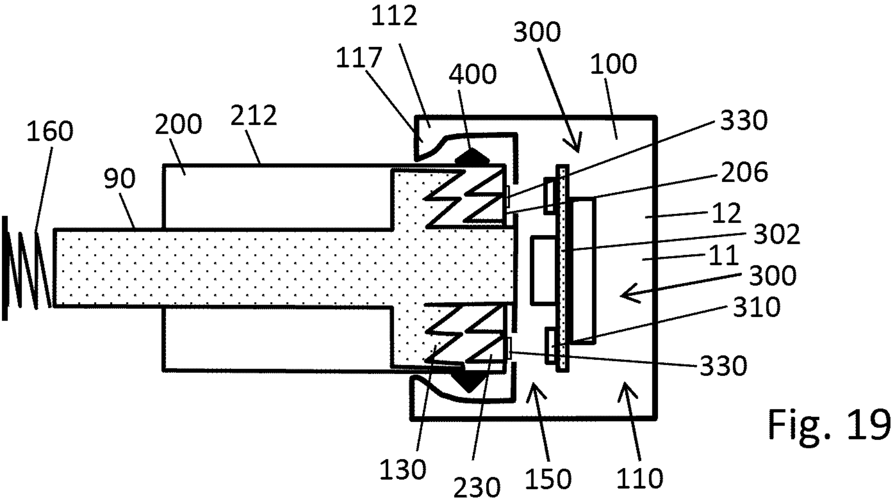
FIG. 19 shows the example of FIG. 18 with the first component in the trigger position.

In FIGS. 18 and 19 another example of first and second components 100, 200 is schematically illustrated. Here, the second component 200 comprises a tubular-shaped sidewall 212 and further comprises a toothed section 230 configured to engage with a correspondingly-shaped toothed section 130 of a clutch 94 of the first component 100. The clutch 90 may be permanently and non-movably fixed to the first component 100. The clutch 90 and/or the first component 100 may be biased in longitudinal direction by the spring 160. The spring 160 may urge the clutch 90 as well as the first component 100 in proximal direction 3 thereby engaging the toothed section 130 of the clutch 90 with the toothed section 230 of the second component 200.

In the initial configuration as illustrated in FIG. 18, in which the toothed sections 130, 230 are in mutual engagement, the first component 100 is rotationally locked to the second component 200. For setting of a dose, both, the first component 100 and the second component 200 may be subject to a rotation relative to the housing 32 or body 10 of the injection device 30. During the dose setting the first and second components 100, 200 may be rotationally locked. They may be also longitudinally locked to each other.

As illustrated in FIGS. 18 and 19, the first component 100 comprises a cup-shaped receptacle 110 formed by a tubular-shaped sidewall at least partially enclosing the tubular shaped or cylindrical sidewall 212 at or near the proximal end of the second component 200. The cup-shaped receptacle 110 is open towards the code 330, which is e.g. provided on a proximally facing end face 206 of the second component 200. The code 330, e.g. implemented as a rotary encoding 332 faces towards the sensor 308, 310 of the electronic detector 300 attached to the first component 100.

Also here, the cavity 150 configured to accommodate both, the electronic detector 300 and the corresponding code 330 is sealed against ingress of impurities through the gasket 400 provided on the outside surface of the second sidewall 212 of the second component 200. In the initial configuration as illustrated in FIG. 18 the gasket 400 is provided in an overlapping section of the first sidewall 112 and the second sidewall 212. The distal end of the first sidewall 112 comprises a radially inwardly extending, e.g. annular protrusion, e.g. in form of a radially inwardly extending bulged section 117 being in axial or longitudinal engagement with the first gasket 400. In this way, the cavity 150 formed in the interface between the first component 100 and the second component 200 is effectively sealed against ingress of impurities.

As the first component is depressed or moved into the trigger position as illustrated in FIG. 19 and as the first component 100 is subject to a distally directed longitudinal displacement relative to the second component 200 as illustrated in FIG. 19, the protruding or inwardly bulged section 117 of the first sidewall 112 separates in distal direction from the gasket 400. At the same time, the toothed section 130 moves out of engagement and decouples from the correspondingly or complementary shaped toothed section 230 and the rotational interlock between the first component 100 and the second component 200 is hence abrogated.

Here, the second component 200 may become free to rotate relative to the first component for and during dispensing of the dose of the medicament.

With the example of FIGS. 18 and 19 the first component 100 has a twofold function it serves to set a dose through dialing or rotating the first component 100 in unison with the second component 200 relative to the housing 32. Moreover, the first component acts and behaves as a trigger 11. It can be depressed in distal direction 2 relative to the second component 200 to initiate dispensing or expelling of the dose.

Figure 20:
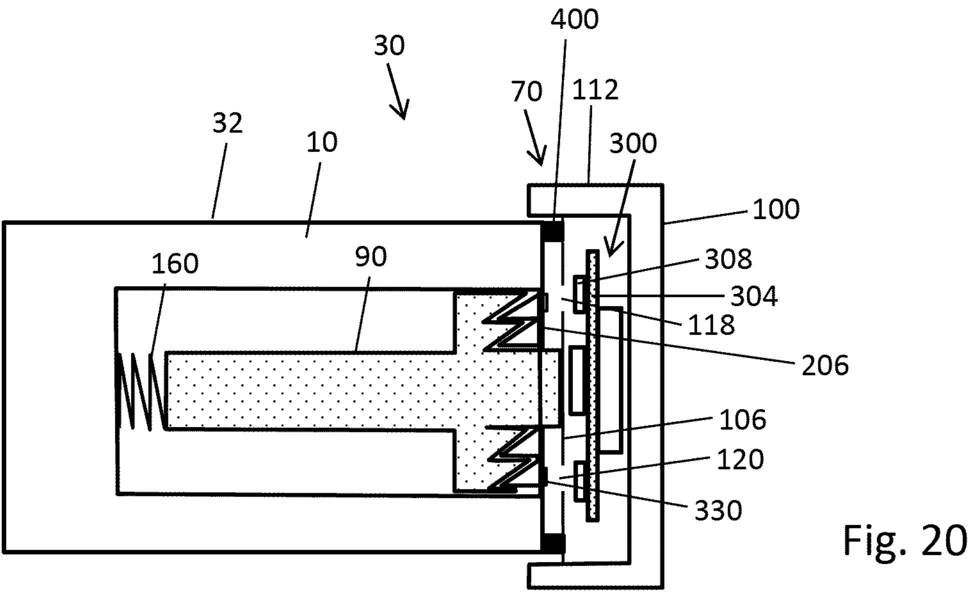
FIG. 20 is illustrative of another example of a first and a second component relative to a housing of an injection device with the first component in an initial position.
Figure 21:
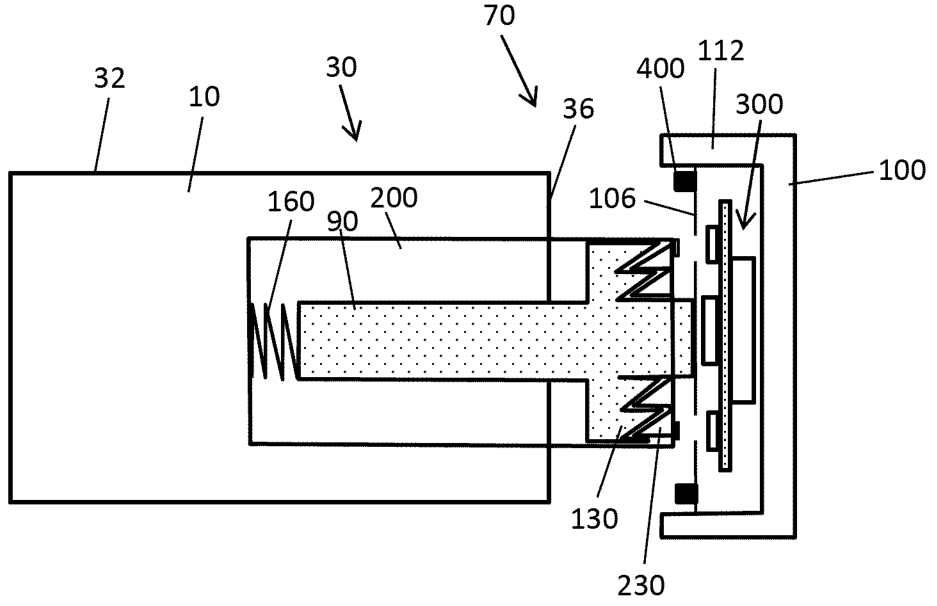
FIG. 21 shows the example of FIG. 20 with the first component being in a trigger position.

The further example as illustrated in FIGS. 20 and 21 is illustrative of a dial extension 70. Here, the first component 100 and the second component 200 constitute or form part of the dial extension 70. The dial extension 70, hence the first component 100 and the second component 200 are displaceable in unison in longitudinal direction relative to the housing 32 or body 10 of the injection device 30. In the initial position of the first component 100 relative to the housing 32, a first gasket 400 effectively seals a cavity 150 provided and confined by the first component 100, the second component 200 and the housing 32. Also here the first component 100 is in axial abutment or is permanently connected and fixed to the clutch 90.

The clutch 90 is longitudinally biased by the return spring 160 relative to the second component 200. As illustrated in FIG. 21 the code 330 is provided on a proximally facing end face 206 of the second component 200 and the electronic detector 300 is located inside a cup-shaped receptacle 110 of the first component 100. The cup-shaped receptacle 100 and may be closed by a distally facing end face 106 in which there is provided at least one aperture 118, 120 to enable an uninterrupted interaction between the at least one sensor 308, 310 of the electronic detector 300 with the code 300 provided on the end face 206.

In the example of FIGS. 20 and 21, the end face 106 is provided with the gasket 400. In the initial position as shown in FIG. 20, the gasket 400 is in sealing axial abutment with the end face 36 of the housing 32. Likewise, the gasket 400 may be also provided on the end face 36 and may get into axial or longitudinal abutment with the end face 106 of the first component.

As shown in FIG. 21 and when the first component 100 is moved into a trigger position for dispensing of the dose of the medicament the sealing engagement between the first component 100 and the housing 32 is abrogated. Here and contrary to the examples as described above in connection with FIGS. 6-19 the trigger position of the first component is proximally offset from the initial position of the first component 100. In the trigger position as illustrated in FIG. 21, the first component is ready to become depressed by a user for initiating or for triggering a dispensing of the dose of the medicament. For dispensing of the dose, the first component 100 is depressed in distal direction 2, thus bringing the toothed sections 130, 230 of the clutch 90 and the second component 200 out of engagement in a way similar as described above in connection with FIG. 19.

Then, the second component 200 is free to rotate relative to the first component 100 and relative to the housing 32. Releasing the first component 100 during dose dispensing or at the end of a dose dispensing procedure leads to a proximally directed displacement of the first component 100 through the spring biased clutch 90 relative to the second component 200 thereby re-engaging the correspondingly-shaped toothed sections 130, 230 and re-establishing of the sealing of the cavity 150.

Figure 22:
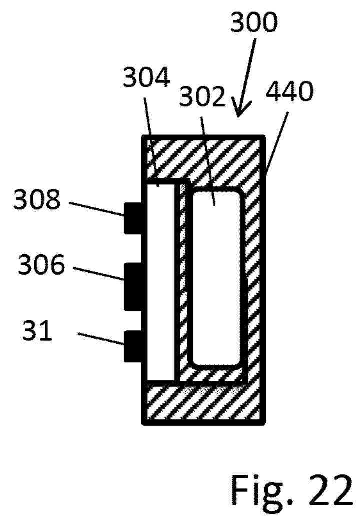
FIG. 22 is illustrative of an example, in which the electronic detector is at least partially encapsulated by a gasket or seal.

In the numerous examples of FIGS. 22-25, the electronic detector 300 may be encapsulated by a gasket 440. Here, the gasket 440 may comprise a sealing resin or may comprise some kind of a potting compound. As illustrated in FIG. 22, the entirety of a proximal portion of the PCB 304 and the battery 302 may be encapsulated by the gasket 440. The sensor is 308, 310 as well as the processor 306 may be provided on a distally facing side of the PCB 304. They may be void of the gasket or may protrude distally from the gasket 440.

Figure 23:
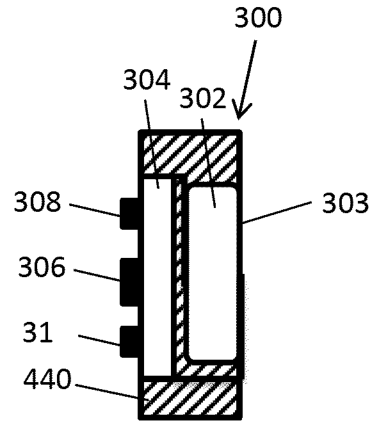
FIG. 23 shows another example of an electronic detector at least partially encapsulated.

With the example of FIG. 23, only the proximal portion as well as the circumferential side section of the PCB 304 and the battery 302 are encapsulated by the gasket 440. A proximal contact surface 303 of the battery is void of the gasket 440.

Figure 24:
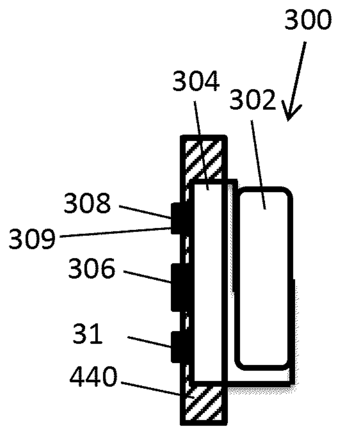
FIG. 24 shows another example of an electronic detector at least partially encapsulated and FIG. 25 shows a further example of an electronic detector being at least partially encapsulated.

With the further example of FIG. 24, the gasket 440 encloses and surrounds only the PCB 304. Here, at least some of the electronic components of the electronic detector 300, e.g. the sensor 308, 310 and/or the processor 306 may be partially surrounded or at least partially encapsulated by the gasket 440. At least a sensing surface or sensing side 309 of the sensors 308, 310 facing away from the PCB 304 is and remains uncovered or protrudes from the gasket 440.

Figure 25:
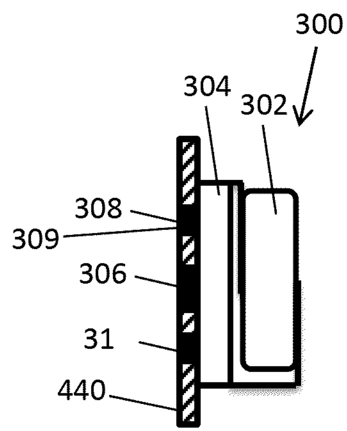

With the further example of FIG. 25, only the electronic components provided on the PCB 304 are encapsulated or embedded in the gasket 440. Here, a sensing or detection surface 309 of the sensors 308, 310 is flush with the gasket 440 and remains uncovered for enabling an unobstructed measurement and detection.

LIST OF REFERENCE NUMBERS

1 drug delivery device
2 distal direction
3 first direction
4 second direction
5 dose decrementing direction
6 cartridge
7 bung
8 fixed window
10 body
11 trigger
12 dose dial
13 dosage window
14 cartridge holder
15 injection needle
16 inner needle cap
17 outer needle cap
18 protective cap
20 piston rod
21 bearing
22 threaded section
23 pressure foot
25 barrel
26 seal
27 medicament
28 socket
30 injection device
32 housing
33 label
34 drive mechanism
36 end face
64 stem
65 external electronic device
66 communication link
70 dial extension
71 sleeve
80 number sleeve
81 groove
90 clutch
92 extension
100 first component
106 end face
110 receptacle
112 sidewall
115 curved section
117 bulged section
118 aperture
120 aperture
122 abutment
130 toothed section
150 cavity
160 spring
200 second component
206 end face
210 receptacle
211 bottom
212 sidewall
215 tapering section
220 counter abutment
230 toothed section
300 electronic detector
302 battery
303 contact surface
304 PCB
306 processor
308 sensor
309 surface
310 sensor
330 code
332 rotary encoding
400 gasket
420 gasket
440 gasket

The invention claimed is:

1. An injection device for administering a dose of a medicament, the injection device comprising:

a housing extending along a longitudinal direction and configured to accommodate a cartridge filled with the medicament;

a drive mechanism configured to operably engage with the cartridge for dispensing the dose of the medicament;

a first component movable relative to the housing along the longitudinal direction between an initial position and a trigger position for dispensing the dose;

a second component rotatable relative to the housing for at least one of setting the dose or dispensing the dose;

a cavity provided in or formed by at least one of the first component or the second component, wherein the cavity is sized to accommodate an electronic detector, wherein one of the first component and the second component is configured for attachment of the electronic detector, and the electronic detector is configured to recognize a code provided on the other one of the first component and the second component; and at least one first gasket fastened to one of the housing, the first component, and the second component, wherein the at least one first gasket is configured to seal the cavity against an ingress of impurities at least while the first component is in the initial position, wherein when the first component is in the trigger position, the at least one first gasket is fastened to one of the housing, the first component, and the second component, and is disengaged from the other two of the housing, the first component, and the second component.

2. The injection device according to claim 1, wherein the second component is rotatable relative to the first component during at least one of setting the dose and dispensing the dose.

3. The injection device according to claim 1, wherein the code comprises a rotary encoding.

4. The injection device according to claim 1, wherein the first component is movable relative to the second component along the longitudinal direction into the trigger position for dispensing the dose.

5. The injection device according to claim 1, wherein when the first component is in the initial position, the at least one first gasket is sealingly engaged with at least two of the housing, the first component, and the second component.

6. The injection device according to claim 1, wherein the second component comprises one of a dose dial and a dial extension rotatable relative to the housing for setting the dose.

7. The injection device according to claim 1, further comprising the cartridge filled with the medicament and arranged inside the housing.

8. The injection device according to claim 1, wherein the drive mechanism includes a clutch, wherein a distal movement of the clutch in the longitudinal direction relative to at least one of the second component or the housing causes switching of the drive mechanism from a dose setting mode to a dose dispensing mode.

9. An injection device for administering a dose of a medicament, the injection device comprising:

a housing extending along a longitudinal direction and configured to accommodate a cartridge filled with the medicament;

a drive mechanism configured to operably engage with the cartridge for dispensing the dose of the medicament;

a first component movable relative to the housing along the longitudinal direction between an initial position and a trigger position for dispensing the dose;

a second component rotatable relative to the housing for at least one of setting the dose or dispensing the dose;

a cavity provided in or formed by at least one of the first component or the second component, wherein the cavity is sized to accommodate an electronic detector, wherein one of the first component and the second component is configured for attachment of the electronic detector, and the electronic detector is configured to recognize a code provided on the other one of the first component and the second component; and at least one first gasket fastened to one of the housing, the first component, and the second component, wherein the at least one first gasket is configured to seal the cavity against an ingress of impurities at least while the first component is in the initial position, wherein the at least one first gasket is provided on one of a proximal end face of the housing and a longitudinal end face of one of the first component and the second component, the at least one first gasket being sealingly engaged with the proximal end face and the longitudinal end face when the first component is in the initial position.

10. The injection device according to claim 9, wherein the second component is rotatable relative to the first component during at least one of setting the dose and dispensing the dose.

11. The injection device according to claim 9, wherein the first component comprises a trigger provided at a proximal end of the injection device and distally depressible in the longitudinal direction for dispensing the dose.

12. The injection device according to claim 9, wherein the second component comprises one of a dose dial and a dial extension rotatable relative to the housing for setting the dose.

13. The injection device according to claim 9, further comprising the cartridge filled with the medicament and arranged inside the housing.

14. The injection device according to claim 9, wherein the drive mechanism includes a clutch, wherein a distal movement of the clutch in the longitudinal direction relative to at least one of the second component or the housing causes switching of the drive mechanism from a dose setting mode to a dose dispensing mode.

15. An injection device for administering a dose of a medicament, the injection device comprising:

a housing extending along a longitudinal direction and configured to accommodate a cartridge filled with the medicament;

a drive mechanism configured to operably engage with the cartridge for dispensing the dose of the medicament;

a first component movable relative to the housing along the longitudinal direction between an initial position and a trigger position for dispensing the dose;

a second component rotatable relative to the housing for at least one of setting the dose or dispensing the dose;

a cavity provided in or formed by at least one of the first component or the second component, wherein the cavity is sized to accommodate an electronic detector, wherein one of the first component and the second component is configured for attachment of the electronic detector, and the electronic detector is configured to recognize a code provided on the other one of the first component and the second component; and at least one first gasket fastened to one of the housing, the first component, and the second component, wherein the at least one first gasket is configured to seal the cavity against an ingress of impurities at least while the first component is in the initial position, wherein the first component comprises a first sidewall, and the second component comprises a second sidewall at least partially surrounding the first sidewall, and wherein the at least one first gasket is sealingly disengaged from at least one of the first sidewall and the second sidewall when the first component is in the trigger position.

16. The injection device according to claim 15, wherein the at least one first gasket is fastened to one of the first sidewall or the second sidewall, and the at least one first gasket faces towards the other one of the first sidewall and the second sidewall.

17. The injection device according to claim 15, wherein the at least one first gasket is attached to one of the first sidewall and the second sidewall, and the at least one first gasket protrudes towards the other one of the first sidewall and the second sidewall.

18. The injection device according to claim 15, wherein at least one of the first sidewall or the second sidewall comprises at least one of a tapering section, a curved section, or a bulged section in the longitudinal direction.

19. The injection device according to claim 15, wherein the at least one first gasket is in a sealing engagement with the first sidewall and with the second sidewall when the first component is in the initial position.

20. The injection device according to claim 1, wherein the first component comprises a trigger provided at a proximal end of the injection device and distally depressible in the longitudinal direction for dispensing the dose.

* * * * *